United States Patent
Larkin et al.

(10) Patent No.: US 9,700,609 B2
(45) Date of Patent: Jul. 11, 2017

(54) COMPOSITIONS FOR TREATMENT AND/OR PREVENTION OF AUTOIMMUNE DISORDERS

(71) Applicant: University of Florida Research Foundation, Incorporated, Gainesville, FL (US)

(72) Inventors: Joseph Larkin, Gainesville, FL (US); Mark A. Atkinson, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 14/774,461

(22) PCT Filed: Mar. 18, 2014

(86) PCT No.: PCT/US2014/031057
§ 371 (c)(1),
(2) Date: Sep. 10, 2015

(87) PCT Pub. No.: WO2014/146097
PCT Pub. Date: Sep. 18, 2014

(65) Prior Publication Data
US 2016/0022793 A1 Jan. 28, 2016

Related U.S. Application Data

(60) Provisional application No. 61/793,321, filed on Mar. 15, 2013.

(51) Int. Cl.
| | |
|---|---|
| *A61K 39/02* | (2006.01) |
| *A61K 38/02* | (2006.01) |
| *A61K 38/08* | (2006.01) |
| *A61K 35/15* | (2015.01) |
| *C07K 7/06* | (2006.01) |
| *C07K 7/08* | (2006.01) |
| *A61K 39/08* | (2006.01) |
| *A61K 39/09* | (2006.01) |
| *A61K 39/00* | (2006.01) |

(52) U.S. Cl.
CPC .............. *A61K 39/02* (2013.01); *A61K 35/15* (2013.01); *A61K 39/0008* (2013.01); *A61K 39/0208* (2013.01); *A61K 39/08* (2013.01); *A61K 39/09* (2013.01); *A61K 2039/5154* (2013.01); *A61K 2039/5158* (2013.01); *A61K 2039/577* (2013.01); *A61K 2039/58* (2013.01)

(58) Field of Classification Search
None
See application file for complete search history.

(56) References Cited

U.S. PATENT DOCUMENTS

| | | |
|---|---|---|
| 2010/0255023 A1 | 10/2010 | Chen |
| 2012/0003239 A1 | 1/2012 | Hyoty et al. |
| 2012/0183513 A1 | 7/2012 | Neu et al. |
| 2012/0258126 A1 | 10/2012 | Schøller et al. |

FOREIGN PATENT DOCUMENTS

EP     1 187 631 B1    3/2002

OTHER PUBLICATIONS

Doti et al (Biochem. J. (2012), 443,231-240 2012).*
Ahmed, Chulbul M. et al., "SOCS-1 Mimetics Protect Mice against Lethal Poxvirus Infection: Identification of a Novel Endogenous Antiviral System," *Journal of Virology*, Feb. 2009, 83(3):1402-1415.
Ahmed, Chulbul M.I. et al., "Enhancement of Antiviral Immunity by Small Molecule Antagonist of Suppressor of Cytokine Signaling," *The Journal of Immunology*, 2010, 185:1103-1113.
Atarashi, Koji et al., "Induction of Colonic Regulatory T Cells by Indigenous *Clostridium* Species," *Science Express*, Dec. 2010, 331:337-341.
Atkinson, M.A et al., "Does the gut microbiota have a role in type 1 diabetes? Early evidence from humans and animal models of the disease," *Diabetologia*, Nov. 2012, 55(11):2868-2877.
Bedoya, Simone Kennedy et al., "Th17 Cells in Immunity and Autoimmunity," *Clinical and Developmental Immunology*, 2013, 2013:1-16.
Belkaid, Yasmine et al., "Tuning Microenvironments: Induction of Regulatory T Cells by Dendritic Cells," *Immunity*, Sep. 2008, 29(3): 362-371.
Bending, David et al., "Highly purified Th17 cells from BDC2. 5NOD mice convert into TH1-like cells in NOD/SCID recipient mice," *The Journal of Clinical Investigation*, Mar. 2009, 119(3):565-572.
Bettelli, Estelle et al., "Reciprocal developmental pathways for the generation of pathogenic effector $T_H17$ and regulatory T cells," *Nature*, May 2006, 441: 235-238.
Bosi, Emanuele et al., "Autoantibody Response to Islet Transplantation in Type 1 Diabetes," *Diabetes*, Nov. 2001, 50:2464-2471.
Brown, Christopher T. et al., "Gut Microbiome Metagenomics Analysis Suggests a Functional Model for the Development of Autoimmunity for Type 1 Diabetes," *PLoS One*, Oct. 2011, 6(10):e25792.

(Continued)

*Primary Examiner* — Oluwatosin Ogunbiyi
(74) *Attorney, Agent, or Firm* — Saliwanchik, Lloyd & Eisenschenk

(57) ABSTRACT

The invention provides compositions for treating or preventing T1D (T1D), the compositions comprising one or more antigen presenting cells (APC) that have been pulsed with one or more bacteria and/or components of the bacteria, wherein the bacteria or their components confer upon the APCs the ability to inhibit the generation of diabetes-promoting T cells. The subject invention also provides a method of treating or preventing T1D in a subject, the method comprising administering APC that have been pulsed with one or more bacteria and/or components of the bacteria and wherein the bacteria or their components confer upon the APCs the ability to inhibit the generation of diabetes-promoting T cells.

3 Claims, 19 Drawing Sheets

(56) References Cited

OTHER PUBLICATIONS

Brugman, S. et al., "Antibiotic treatment partially protects against type 1 diabetes in the Bio-Breeding diabetes-prone ret. Is the gut flora involved in the development of type 1 diabetes?," *Diabetologia*, 2006, 49:2105-2108.

Butler, Matt et al., "Altered Expression and endocytic function of CD205 in human dendritic cells, and detection of CD205-DCL-1 fusion protein upon dendritic cell maturation," *Immunology*, 2006, 120:362-371.

Calcinaro, F. et al., "Oral probiotic administration induces interleukin-10 production and prevents spontaneous autoimmune diabetes in the non-obese diabetic mouse," *Diabetologia*, 2005, 45:1565-1575.

Curtis, Meredith M. et al., "Interleukin-17 in host defence against bacterial, mycobacterial and fungal pathogens," *Immunology*, 2009, 126:177-185.

Fukaya, Tomohiro et al., "Conditional ablation of CD205+ conventional dendritic cells impacts the regulation of T-cell immunity and homeostasis in vivo," *Proceeding of the National Academy of Sciences of the United States of America*, 2012, 109(28):11288-11293.

Ganda, O.P. et al., "Differential sensitivity to beta-cell secretagogues in "early" type I diabetes mellitus," *Diabetes*, 1984, 33(6):Abstract.

Ghosh, S. et al., "Probiotics in inflammatory bowel disease: is it all gut flora modulation?" *Gut*, 2004, 53:620-622.

Giongo, Adriana et al., "Toward defining the autoimmune microbiome for type 1 diabetes," *International Society for Microbial Ecology Journal*, 2010, 1-10.

Graham, S. et al., "Enteropathy precedes type 1 diabetes in the BB rat," *Gut*, 2004, 53:1437-1444.

Grainger, John et al., "Microbe-dendritic cell dialogue controls regulatory T-cell fate," *Immunology Review*, Mar. 2010, 234(1):305-316.

Grinberg-Bleyer, Yenkel et al., "IL-2 reverses established type 1 diabetes in NOD mice by a local effect on pancreatic regulatory T cells," *The Journal of Experimental Medicine*, 2010, 207(9):1871-1878.

Happel, Kyle I. et al., "Divergent roles of IL-23 and IL-12 in host defense against *Klebsiella pneumoniae*," *The Journal of Experimental Medicine*, 2005, 202(6):761-769.

Higgins, Sarah C. et al., "TLR4 Mediates Vaccine-Induced Protective Cellular Immunity to *Bordetella pertussis*: Role of IL-17-Producing T Cells," *The Journal of Immunology*, 2006, 177:7980-7989.

Hyttinen, Valma et al., "Genetic Liability of Type 1 Diabetes and the Onset Age Among 22,650 Young Finnish Twin Pairs: A Nationwide Follow-Up Study," *Diabetes*, 2003, 52:1052-1055.

Ivanov, Ivaylo Ivanov et al., "Specific microbiota direct the differentiation of Th17 cells in the mucosa of the small intestine," *Cell Host Microbe*, Oct. 2008, 4(4):337-349.

Jacob, Chaim O. et al., "Prevention of diabetes in nonobese diabetic mice by tumor necrosis factor (TNF): Similarities between TNF-α and interleukin 1," *Proceedings of the National Academy of Sciences of the United States of America*, 1990, 87:968-972.

Jager, Lindsey D. et al., "The Kinase Inhibitory Region of SOCS-1 is Sufficient to Inhibit T-helper 17 and other Immune Functions in Experimental Allergic Encephalomyelitis," *Journal of Neuroimmunology*, 2011, 232:108-118.

Kawasaki, Eiji et al., "High-Throughput Radioassays for Autoantibodies to Recombinant Autoantigens," *Frontiers in Bioscience*, Nov. 2000, 5:E181-E190.

Kingma, Sandra D.K. et al., "*Lactobacillus johnsonii* N6.2 Stimulates the Innate Immune Response through Toll-Like Receptor 9 in Caco-2 Cells and Increases Intestinal Crypt Paneth Cell Number in BioBreeding Diabetes-Prone Rats," *The Journal of Nutrition*, 2011, 141:1023-1028.

Kriegel, Martin A. et al., "Naturally transmitted segmented filamentous bacteria segregate with diabetes protection in nonobese diabetic mice," *Proceedings of the National Academy of Sciences*, 2011, 108(28):11548-11553.

Kunisawa, Jun et al., "Peaceful Mutualism in the Gut: Revealing Key Commensal Bacteria for the Creation and Maintenance of Immunological Homeostasis," *Cell Host and Microbe*, 2011, 9:83-84.

Lagasse, James M. et al., "Successful Prospective Prediction of Type 1 Diabetes in Schoolchildren Through Multiple Defined Autoantibodies," *Diabetes Care*, 2002, 25(3):505-511.

Larkin III, Joseph et al., "Regulation of interferon gamma signaling by suppressors of cytokine signaling and regulatory T cells," *Frontiers in Immunology*, 2013, 4(469):1-8.

Lau, Kenneth et al., "Inhibition of Type 1 Diabetes Correlated to a *Lactobacillus johnsonii* N6.2-Mediated Th17 Bias," *The Journal of Immunology*, 2011, 186:3538-3546.

Like, Arthur A. et al., "Influence of Environmental Viral Agents on Frequency and Tempo of Diabetes Mellitus in BB/Wor Rats," *Diabetes*, Feb. 1991, 40(2):Abstract.

Martin-Orozco, Natalia et al., "Th17 cells promote pancreatic inflammation but only induce diabetes efficiently in lymphopenic hosts after conversion into Th1 cells," *European Journal of Immunology*, 2009, 39(1):216-224.

Matsuzaki, T. et al., "Prevention of onset in an insulin-dependent diabetes mellitus model, NOD mice, by oral feeding of *Lactobacillus casei*," *APMIS*, Aug. 1997, 105(8):Abstract.

McInerney, M.F. et al., "Prevention of insulitis and diabetes onset by treatment with complete Freund's adjuvant in NOD mice," *Diabetes*, Jun. 1991, 40(6):Abstract.

Meddings, J.B. et al., "Increased gastrointestinal permeability is an early lesion in the spontaneously diabetic BB rat," *American Physiological Society*, 1999, 276:G951-G957.

Metcalfe, Karl A. et al., "Concordance for Type 1 Diabetes in Identical Twins is Affected by Insulin Genotype," *Diabetes Care*, 2001, 24(5):838-842.

Murphy, Craig A. et al., "Divergent Pro-Anti-inflammatory Roles for IL-23 and IL-12 in Joint Autoimmune Inflammation," *The Journal of Experimental Medicine*, 2003, 198(12):1951-1957.

Neu, Josef et al., "Changes in Intestinal Morphology and Permeability in the BioBreeding Rat Before the Onset of Type 1 Diabetes," *Journal of Pediatric Gastroenterology and Nutrition*, 2005, 40:589-595.

Nikoopour, Enayat et al., "Th17 Polarized Cells from Nonobese Diabetic Mice Following Mycobacterial Adjuvant Immunotherapy Delay Type 1 Diabetes," *Journal of Immunology*, 2010, 184:4779-4788.

Ouyang, Wenjun et al., "The Biological Functions of T Helper 17 Cell Effector Cytokines in Inflammation," *Immunity*, 2008, 28(4):454-467.

Pyke, D.A. "Diabetes: the genetic connections," *Diabetologia*, Dec. 1979, 17(6):Abstract.

Redondo, M.J. et al., "Heterogeneity of Type 1 diabetes: analysis of monozygotic twins in Great Britain and the United States," *Diabetologia*, 2001, 44:354-362.

Roesch, Luiz F.W. et al., "Culture-independent identification of gut bacteria correlated with the onset of diabetes in a rat model," *The ISME Journal*, 2009, 1-13.

Round, June L. et al., "Inducible Foxp3+ regulatory T-cell development by a commensal bacterium of the intestinal microbiota," *Proceedings of the National Academy of Sciences*, 2010, 107(27):12204-12209.

Round, June L. et al., "The gut microbiota shapes intestinal immune responses during health and disease," *Nature Reviews Immunology*, 2009, 9:313-323.

Rubinstein, P. et al., "HLA antigens and islet cell antibodies in gestational diabetes," *Hum Immunol*, Nov. 1981, 3(3):271-275.

Sacks, David B. et al., "Molecular Manipulation of Autoantibody Testing in Type 1 Diabetes: Two for One," *Clinical Chemistry*, 2001, 47(5):803-804.

Sadelain, M.W. et al., "Prevention of diabetes in the BB rat by early immunotherapy using Freund's adjuvant," *J Autoimmun*, Dec. 1990, 3(6):671-680.

(56) References Cited

OTHER PUBLICATIONS

Sadelain, M.W. et al., "Prevention of type 1 diabetes in NOD mice by adjuvant immunotherapy," *Diabetes*, Dec. 1990, 39(5):Abstract.
Sartorius, Rossella et al., "Vaccination with filamentous bacteriophages targeting DEC-205 induces DC maturation and potent anti-tumor T-cell responses in the absence of adjuvants," *European Journal of Immunology*, 2011, 41:2573-2584.
Schwartz, R.F. et al., "Comment on: Brugman S et al. (2006) Antibiotic treatment partially protects against type 1 diabetes in the Bio-Breeding diabetes-prone rat. Is the gut flora involved in the development of type 1 diabetes?," *Diabetologia*, 2007, 50:220-221.
Serreze, David V. et al., "Use of Recombinant Congenic and Congenic Strains of NOD Mice to Identify a New Insulin-dependent Diabetes Resistance Gene," *The Journal of Experimental Medicine*, 1994, 180:1553-1558.
Shoda, Lisl K.M. et al., "A Comprehensive Review of Interventions in the NOD Mouse and Implications for Translation," *Immunity*, 23:115-126.
Shrimpton, Rachel E. et al., "CD205 (DEC-205): A recognition receptor for apoptotic and necrotic self," *Molecular Immunology*, 2009, 46:1229-1239.
Srikanta, S. et al., "Pre-type 1 diabetes. Linear loss of beta cell response to intravenous glucose," Diabetes, Aug. 1984, 33(8):Abstract.
Stratmann, Thomas et al., "Susceptible MHC alleles, not background genes, select an autoimmune T cell reactivity," *The Journal of Clinical Investigation*, 2003, 112(6): 902-914.

Tse, Hubert M. et al., "NADPH Oxidase Deficiency Regulates Th Lineage Commitment and Modulates Autoimmunity," *Journal of Immunology*, 2010, 185(9):5247-5258.
Turley, Shannon J. et al., "Endocrine self and gut non-self intersect in the pancreatic lymph nodes," *Proceedings of the National Academy of Sciences*, 2005, 102(49):17729-17733.
Vaarala, Outi et al., "The "Perfect Storm" for Type 1 Diabetes: The Complex Interplay Between Intestinal Microbiota, Gut Permeability, and Mucosal Immunity," *Diabetes*, 2008, 57:2555-2562.
Valladares, Ricardo et al., "*Lactobacillus johnsonii* N6.2 Mitigates the Development of Type 1 Diabetes in BB-DP Rats," *PLoS One*, 2010, 5(5):e10507.
Verdaguer, Joan et al., "Two Mechanisms for the Non-MHC-Linked Resistance to Spontaneous Autoimmunity," *The Journal of Immunology*, 1999, 162:4614-4626.
Waiboci, Lilian W. et al., "Both the Suppressor of Cytokine Signaling 1 (SOCS-1) Kinase Inhibitory Region and SOCS-1 Mimetic Bind to JAK2 Autophosphorylation Site: Implications for the Development of a SOCS-1 Antagonist," *The Journal of Immunology*, 2007, 178:5058-5068.
Wicker, Linda S. et al., "Genetic Control of Diabetes and Insulitis in the Nonobese Diabetic (NOD) Mouse," *The Journal of Experimental Medicine*, 1987, 165:1639-1654.
Yadav, Hariom et al., "Antidiabetic effect of probiotic dahi containing *Lactobacillus acidophilus* and *Lactobacillus casei* in high fructose fed rats," *Nutrition*, Jan. 2007, 23(1):62-68.

\* cited by examiner

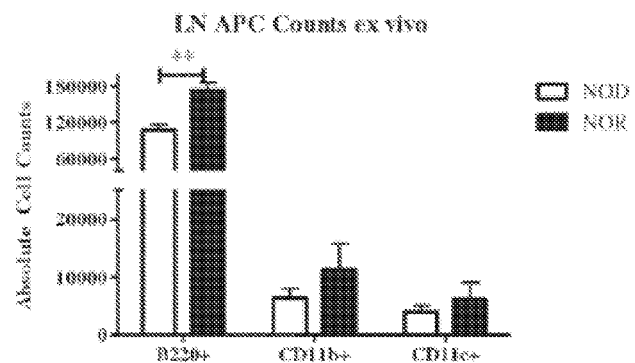
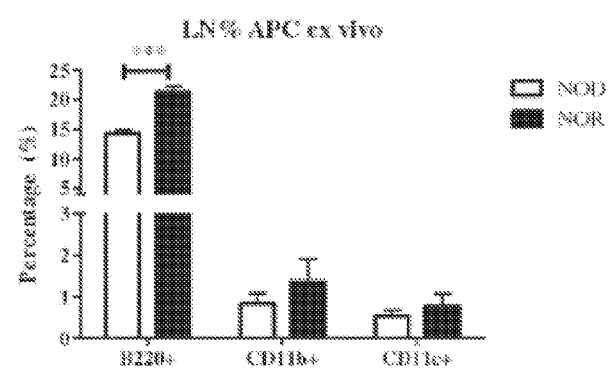
FIG. 2B
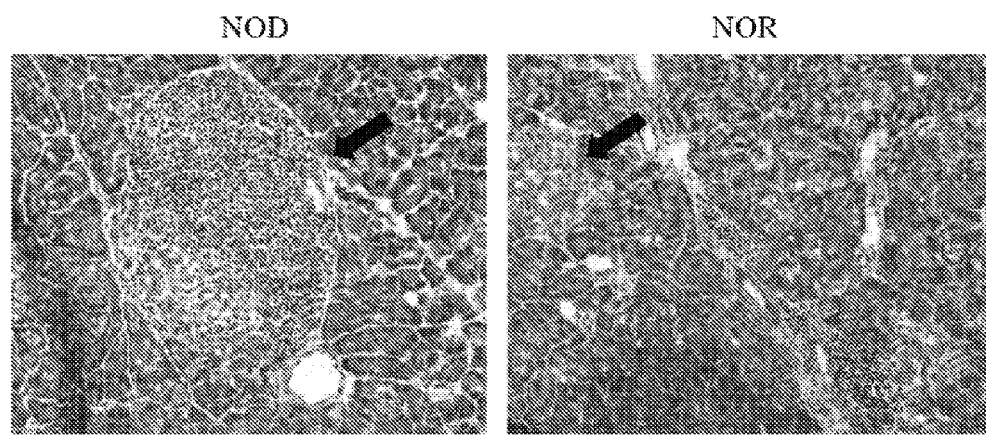
FIG. 3A

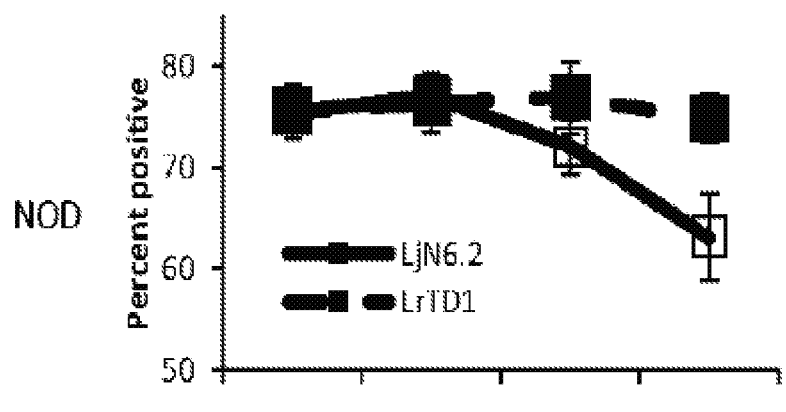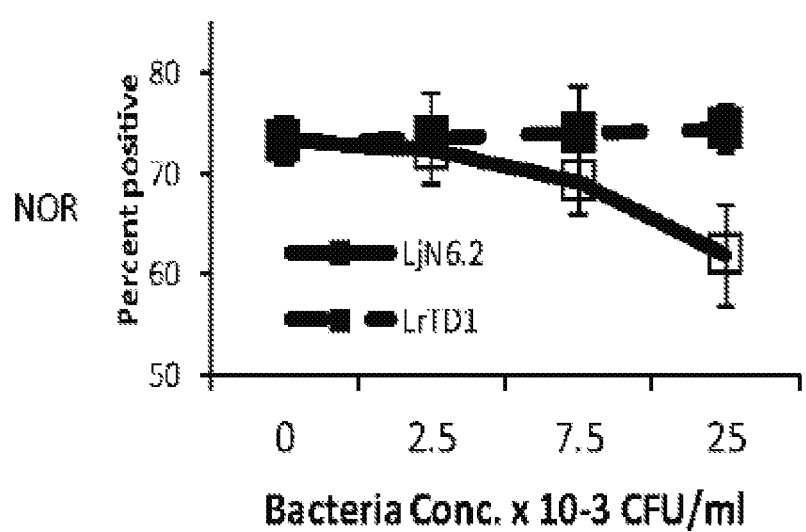
FIG. 9B

| PHYLUM | OTU 97.5% | IL23R | RORγT | IL23 | More abundant in: (p-value) | Average abundance (%) (±sd) NOR | NOD |
|---|---|---|---|---|---|---|---|
| Firmicutes | Clostridium septicum | + | | | NOR (0.021) | 0.76 (±0.44) | 0.07 (±0.06) |
| | unidentified Clostridium | | + | | NOD (0.011) | 2.56 (±0.24) | 4.99 (±0.55) |
| | Clostridium alkalicellulosi | | + | | NOD (0.029) | 0.07 (±0.01) | 0.59 (±0.31) |
| | Clostridium rectum | | | | NOR (0.034) | 0.34 (±0.16) | 0.02 (±0.00) |
| | Clostridium proteolyticum | | | | NOD (0.045) | 0.00 (±0.00) | 0.18 (±0.15) |
| | Clostridium collagenovorans | | | | NOD (0.002) | 0.00 (±0.00) | 0.19 (±0.06) |
| | Clostridium cochlearium | | - | | NOD (0.136) | 0.08 (±0.00) | 0.41 (±0.47) |
| | Eubacterium dolichum | | | | NOD (0.020) | 0.46 (±0.09) | 0.36 (±0.26) |
| | Eubacterium ventriosum | | | | NOD (0.014) | 0.07 (±0.02) | 0.49 (±0.22) |
| | Eubacterium pectini | + | | | NOR (0.230) | 0.54 (±0.48) | 0.18 (±0.15) |
| | Eubacterium tarantellae | | + | | NOR (0.073) | 0.36 (±0.16) | 0.14 (±0.010) |
| | unidentified Syntrophococcus | | | | NOD (0.007) | 0.00 (±0.01) | 0.11 (±0.01) |
| | Ruminococcus gauvreauii | | + | | NOR (0.115) | 0.13 (±0.07) | 0.04 (±0.00) |
| | Ruminococcus lactaris | | - | | NOD (0.082) | 0.07 (±0.00) | 1.06 (±0.91) |
| | Catellicoccus marimammalium | + | | | NOR (0.057) | 1.94 (±0.46) | 0.49 (±0.20) |
| | Candidatus Arthromitus | | - | | NOD (0.095) | 0.05 (±0.02) | 0.10 (±0.04) |
| Bacteroidetes | unidentified Bacteroidales | | | | NOR (0.002) | 0.18 (±0.11) | 0.01 (±0.00) |
| | Blautia stercoris | | | | NOR (0.094) | 1.09 (±1.00) | 0.04 (±0.04) |
| | Porphyromonas levii | | | | NOR (0.017) | 0.64 (±0.95) | 0.00 (±0.00) |
| | Flavobacterium caeni | + | | | NOR (0.023) | 0.71 (±0.29) | 0.07 (±0.07) |
| | Ruminofilibacter xylanolyticum | | + | + | NOR (0.056) | 1.19 (±0.40) | 0.29 (±0.19) |
| | Bacteroidetes symbiont | | - | | NOD (0.149) | 0.89 (±0.18) | 2.01 (±1.12) |
| Proteobacteria | Candidatus Magnetomorum | | + | | NOR (0.088) | 0.25 (±0.09) | 0.00 (±0.01) |

FIG. 11

SEQUENCE LISTING

```
<160> NUMBER OF SEQ ID NOS: 24

<210> SEQ ID NO 1
<211> LENGTH: 20
<212> TYPE: DNA
<213> ORGANISM: Mus musculus

<400> SEQUENCE: 1
ccttccttct tgggtatgca                                                   20

<210> SEQ ID NO 2
<211> LENGTH: 20
<212> TYPE: DNA
<213> ORGANISM: Mus musculus

<400> SEQUENCE: 2
ggaggagcaa tgatcttgat                                                   20

<210> SEQ ID NO 3
<211> LENGTH: 20
<212> TYPE: DNA
<213> ORGANISM: Mus musculus

<400> SEQUENCE: 3
ccacagcact gtagggttta                                                   20

<210> SEQ ID NO 4
<211> LENGTH: 23
<212> TYPE: DNA
<213> ORGANISM: Mus musculus

<400> SEQUENCE: 4
attgtctttc ttctgccgtt ctc                                               23
```

-continued

<210> SEQ ID NO 5
<211> LENGTH: 20
<212> TYPE: DNA
<213> ORGANISM: Mus musculus

<400> SEQUENCE: 5
gacctgacag cagtagccat                                           20

<210> SEQ ID NO 6
<211> LENGTH: 20
<212> TYPE: DNA
<213> ORGANISM: Mus musculus

<400> SEQUENCE: 6
ctccttgttt tgccctgtgg                                           20

<210> SEQ ID NO 7
<211> LENGTH: 23
<212> TYPE: DNA
<213> ORGANISM: Mus musculus

<400> SEQUENCE: 7
aactatttta actcaagtgg cat                                       23

<210> SEQ ID NO 8
<211> LENGTH: 18
<212> TYPE: DNA
<213> ORGANISM: Mus musculus

<400> SEQUENCE: 8
aggtgtgatt caatgacg                                             18

<210> SEQ ID NO 9
<211> LENGTH: 22
<212> TYPE: DNA
<213> ORGANISM: Mus musculus

<400> SEQUENCE: 9
ggaaatgaga aaagagttgt gc                                        22

<210> SEQ ID NO 10
<211> LENGTH: 21
<212> TYPE: DNA
<213> ORGANISM: Mus musculus

<400> SEQUENCE: 10
ctccagaaga ccagaggaaa t                                         21

<210> SEQ ID NO 11
<211> LENGTH: 17
<212> TYPE: DNA
<213> ORGANISM: Mus musculus

<400> SEQUENCE: 11
gctctctcgg aatctct                                              17

<210> SEQ ID NO 12
<211> LENGTH: 19
<212> TYPE: DNA
<213> ORGANISM: Mus musculus

<400> SEQUENCE: 12
aagcagaact ggctgttgt                                            19

```
<210> SEQ ID NO 13
<211> LENGTH: 24
<212> TYPE: DNA
<213> ORGANISM: Mus musculus

<400> SEQUENCE: 13
tgaaagagac cctacatccc ttga                                               24

<210> SEQ ID NO 14
<211> LENGTH: 26
<212> TYPE: DNA
<213> ORGANISM: Mus musculus

<400> SEQUENCE: 14
cagaaaattg gaagttggga tatgtt                                             26

<210> SEQ ID NO 15
<211> LENGTH: 17
<212> TYPE: DNA
<213> ORGANISM: Mus musculus

<400> SEQUENCE: 15
actctccacc gcaatga                                                       17

<210> SEQ ID NO 16
<211> LENGTH: 17
<212> TYPE: DNA
<213> ORGANISM: Mus musculus

<400> SEQUENCE: 16
ctcttcagga ccaggat                                                       17

<210> SEQ ID NO 17
<211> LENGTH: 22
<212> TYPE: DNA
<213> ORGANISM: Mus musculus

<400> SEQUENCE: 17
acagccactg cattcccagt tt                                                 22

<210> SEQ ID NO 18
<211> LENGTH: 22
<212> TYPE: DNA
<213> ORGANISM: Mus musculus

<400> SEQUENCE: 18
tctcggaagg acttgcagac at                                                 22

<210> SEQ ID NO 19
<211> LENGTH: 16
<212> TYPE: PRT
<213> ORGANISM: Artificial sequence
<220> FEATURE:
<223> OTHER INFORMATION: SOCS1-KIR peptide

<400> SEQUENCE: 19

Asp Thr His Phe Arg Thr Phe Arg Ser His Ser Asp Tyr Arg Arg Ile
1               5                   10                  15

<210> SEQ ID NO 20
<211> LENGTH: 16
<212> TYPE: PRT
<213> ORGANISM: Artificial sequence
```

```
<220> FEATURE:
<223> OTHER INFORMATION: SOCS1-KIR2A peptide

<400> SEQUENCE: 20

Asp Thr His Ala Arg Thr Ala Arg Ser His Ser Asp Tyr Arg Arg Ile
1               5                   10                  15

<210> SEQ ID NO 21
<211> LENGTH: 12
<212> TYPE: PRT
<213> ORGANISM: Artificial sequence
<220> FEATURE:
<223> OTHER INFORMATION: tyrosine kinase inhibitory peptide (TKIP)

<400> SEQUENCE: 21

Trp Leu Val Phe Phe Val Ile Phe Tyr Phe Phe Arg
1               5                   10

<210> SEQ ID NO 22
<211> LENGTH: 33
<212> TYPE: PRT
<213> ORGANISM: Artificial sequence
<220> FEATURE:
<223> OTHER INFORMATION: SOCS1-KIR dimer
<220> FEATURE:
<221> NAME/KEY: MISC_FEATURE
<222> LOCATION: (17)..(17)
<223> OTHER INFORMATION: spacer peptide

<400> SEQUENCE: 22

Asp Thr His Phe Arg Thr Phe Arg Ser His Ser Asp Tyr Arg Arg Ile
1               5                   10                  15

Xaa Asp Thr His Phe Arg Thr Phe Arg Ser His Ser Asp Tyr Arg Arg
                20                  25                  30

Ile

<210> SEQ ID NO 23
<211> LENGTH: 13
<212> TYPE: PRT
<213> ORGANISM: Artificial sequence
<220> FEATURE:
<223> OTHER INFORMATION: JAK2(1001-1013) peptide

<400> SEQUENCE: 23

Leu Pro Gln Asp Lys Glu Tyr Tyr Lys Val Lys Glu Pro
1               5                   10

<210> SEQ ID NO 24
<211> LENGTH: 13
<212> TYPE: PRT
<213> ORGANISM: Artificial sequence
<220> FEATURE:
<223> OTHER INFORMATION: pJAK2(1001-1013) peptide
<220> FEATURE:
<221> NAME/KEY: MOD_RES
<222> LOCATION: (7)..(7)
<223> OTHER INFORMATION: PHOSPHORYLATION

<400> SEQUENCE: 24

Leu Pro Gln Asp Lys Glu Tyr Tyr Lys Val Lys Glu Pro
1               5                   10
```

COMPOSITIONS FOR TREATMENT AND/OR PREVENTION OF AUTOIMMUNE DISORDERS

CROSS-REFERENCE TO A RELATED APPLICATIONS

This application is a National Stage Application of International Application Number PCT/US2014/031057, filed Mar. 18, 2014, which claims the benefit of U.S. provisional application Ser. No. 61/793,321, filed Mar. 15, 2013, both of which are incorporated herein by reference in their entirety.

The Sequence Listing for this application is labeled SeqList-18Mar14_ST25.txt which was created on Mar. 18, 2014 and is 5 KB. The entire content of the sequence listing is incorporated herein by reference in its entirety.

BACKGROUND

Diabetes mellitus is a family of disorders characterized by chronic hyperglycemia and the development of long-term vascular complications. This family of disorders includes type 1 diabetes (T1D), type 2 diabetes, gestational diabetes, and other types of diabetes.

Immune-mediated (type 1) diabetes (or insulin dependent diabetes mellitus, IDDM, T1D) is a disease of children and adults for which there currently is no adequate means for prevention or cure. T1D represents approximately 10% of all human diabetes. The disease is characterized by an initial leukocyte infiltration into the pancreas that eventually leads to inflammatory lesions within islets via a process called "insulitis."

T1D is distinct from non-insulin dependent diabetes (NIDDM) in that only the T1D form involves specific destruction of the insulin producing beta cells of the islets of Langerhans. The destruction of beta cells appears to be a result of specific autoimmune attack, in which the patient's own immune system recognizes and destroys the beta cells, but not the surrounding alpha cells (glucagon producing) or delta cells (somatostatin producing) that comprise the pancreatic islet. The progressive loss of pancreatic beta cells results in insufficient insulin production and, thus, impaired glucose metabolism with attendant complications.

The factors responsible for T1D are complex and thought to involve a combination of genetic, environmental, and immunologic influences that contribute to the inability to provide adequate insulin secretion to regulate glycemia.

The natural history of T1D prior to clinical presentation has been extensively studied in search of clues to the etiology and pathogenesis of beta cell destruction. The prediabetic period may span only a few months (e.g., in very young children) to years (e.g., older children and adults). The earliest evidence of beta cell autoimmunity is typically the appearance of various islet autoantibodies. Metabolically, the first signs of abnormality can be observed through intravenous glucose tolerance testing (IVGTT). Later, as the disease progresses, the oral glucose tolerance test (OGTT) typically becomes abnormal. T1D manifests with continued beta cell destruction and insulinopenia.

T1D occurs predominantly in genetically predisposed subjects. Concordance for T1D in identical twins is 30-50% with an even higher rate of concordance for beta cell autoimmunity, as evidenced by the presence of islet autoantibodies in these individuals (Pyke, (1979)). While these data support a major genetic component in the etiopathogenesis of T1D, environmental or non-germline genetic factors must also play important pathologic roles. Environmental factors proposed to date include viral infections, diet (e.g., nitrosamines in smoked meat, infant cereal exposure), childhood vaccines, lack of breast-feeding, early exposure to cows' milk, and aberrant intestinal functioning (Vaarala et al. (2008)). Hence, while the list of potential environmental agents for T1D is large, the specific environmental trigger(s) that precipitate beta cell autoimmunity remain elusive.

Although pre-diabetogenic T cells (bearing TCR specificity for pancreatic islet cell related antigens) are essential for T1D onset, studies in rodent models (Shoda et al. 2005) and patients (Metcalfe et al. (2001); Redondo et al. (2001); Hyttinen et al. (2003)) suggest that T1D may be prevented by inhibiting their acquisition of diabetogenic effector functions. Antigen presenting cells (APC), in particular dendritic cells (DC), maintain immune homeostasis by providing signals sufficient to activate pathogen-specific naïve T lymphocytes while being able to induce tolerance in naïve T cells specific to self-tissues and commensal bacteria. APC modulate immune responses by providing antigen presentation, necessary co-stimulatory signals, and appropriate cytokine environment.

A peaceful mutualism exists between resident gut bacteria and the mammals in which they reside: the host provides food for the commensal bacteria, which in turn provide nutrients to the host by metabolizing otherwise indigestible food. In addition, a dynamic equilibrium also exists between resident gut flora and the development of the mammalian immune system. In particular, Th17 effector functions are induced by resident commensal bacteria, and subsequently regulate the composition of bacteria residing within the gut (Curtis et al. (2009) and Ivanov et al. (2008)).

Studies have shown that modulation of gut composition can alter onset of T1D (Vaarala et al. (2008)). Moreover, it has been recently demonstrated that distinct, naturally occurring microbial communities reside within the gut of Bio-breeding diabetes prone (BBDP) and Bio-breeding diabetes resistant (BBDR) rats (Roesch et al. (2009), and within the subset of female non-obese diabetic (NOD) mice naturally resistant to T1D compared to susceptible syngeneic mice (Kriegel et al. (2011)).

In terms of gut microbial regulation, APC prime T lymphocyte effector functions, maintain mutualistic communities while eliminating those perceived as pathogens. While IL17A (hereafter, IL17) effector function by T lymphocytes is important in microbial gut community regulation (Happel et al. (2005); Higgins et al. (2006); Murphy et al. (2003)), the role of APC primed IL17 production in the context of T1D, is less clear as it has been correlated with both onset and resistance (Nikoopour et al. (2010); Bending et al. (2009); Martin-Orozco et al. (2009)).

Notably, increased natural segregation of gut residing Segmented Filamentous Bacteria (SFB) (Kriegel et al. (2011)) and oral feeding of *Lactobacillus johnsonii* N6.2 (LjN6.2) (Valladares et al. (2010)) were sufficient to confer T1D resistance to T1D susceptible rodent strains. The resistance to T1D mediated by LjN6.2 and SFB was correlated to a Th17 bias (Kriegel et al. (2011); Lau K et al. (2010)). Although DC prime naïve T lymphocytes can interact with resident gut flora communities directly (Grainger et al. (2010)), how distinct microbes can contribute to APC priming of diabetogenic T lymphocytes effector functions is poorly understood.

The NOD is a well-established mouse model of T1D, with destructive leukocytic infiltration of pancreatic islets, followed by insulin insufficiency in >80% of females. The NOR mouse, a recombinant congenic mouse strain, possesses 88% genetic identity with the NOD mouse and also develops leukocytic infiltrations within the pancreatic vasculature. However, unlike NOD mice, the leukocytic infiltrations in NOR do not typically progress to insulitis (i.e., intra-islet invasion), rendering NOR mice T1D free.

As noted above, one of the numerous factors that have been considered in the context of unraveling the complex etiology of T1D is intestinal functioning, including the interaction of intestinal microflora. The presence of a commensal intestinal microbiota in infancy is critical and well documented for numerous physiologic processes including growth, angiogenesis, optimization of nutrition, and stimulation of various arms of the innate and adaptive immune systems. However, similar studies in T1D are limited. In rodent models of T1D, the disease is likely to develop under germ free conditions. Diabetes prone rats (BB-DP) subjected to cesarean derivation develop accelerated disease (Like et al. (1991)). In terms of using such information to proactively modulate diabetes formation, antibiotic treatments to BB-DP rats after weaning (Brugman et al. (2006)) prevents diabetes, whereas with the NOD mouse, a decreased frequency of T1D was observed with the administration of doxycycline (Schwartz et al. (2007)). Probiotic treatment of NOD mice prevents the onset of T1D (Calcinaro et al. (2005); Yadav et al. (2007)). Similarly, a low fat diet with *Lactobacillus* strains reduced insulin-dependent diabetes in rats (Matsuzuki et al. (2007)). Antibiotics can prevent T1D in diabetes-prone rats (Brugman et al. (2006)) and in NOD mice (Schwartz et al. (2006)). The incidence of diabetes in NOD mice increases in a germ-free environment (Suzuki et al. (1987); Wicker et al. (1987)). Freund's adjuvant, which contains mycobacteria, also protects NOD mice and the BB-DP rat against diabetes (Sadelain et al. (1990 a and b) and McInerney et al. (1991)). The specific mechanisms of how such therapies modulate disease are unclear.

T1D is currently managed by the administration of exogenous human recombinant insulin. Although insulin administration is effective in achieving some level of euglycemia in most patients, it does not prevent the long-term complications of the disease including ketosis and damage to small blood vessels, which may affect eyesight, kidney function, and blood pressure and can cause circulatory system complications.

Although knowledge of the immune system has become much more extensive in recent years, the precise etiology of T1D remains a mystery. Furthermore, despite the enormously deleterious health and economic consequences, and the extensive research effort, there currently is no effective means for controlling the formation of this disease.

In addition to T1D, other autoimmune diseases, for example, lupus, multiple sclerosis, inflammatory bowel disease, rheumatoid arthritis, etc. also have a genetic component and an environmental component. One of those environmental components is the interaction between bacteria residing in a subject's body with the subject's immune system. These interactions initially involve the dendritic cells. In addition, autoimmune diseases are promoted by T lymphocytes that acquire autoimmune effector functions, usually mediated through interactions with antigen presenting cells, for example, dendritic cells, and the environment generated by them. The contributions of the environmental factors have not been studied to extent that they can be used in prevention and/or treatment of the autoimmune diseases.

BRIEF SUMMARY

The subject invention provides compositions for treating and/or preventing type 1 diabetes (T1D) and/or other autoimmune disorders. In preferred embodiments, the compositions comprise one or more antigen presenting cells (APC) that have been pulsed with one or more bacteria and/or components of bacteria. The bacteria used to pulse the APC confer upon the APC the ability to inhibit the generation of, for example, diabetes-promoting T-cells. In specific embodiments, these bacteria can be, for example, *Eubacteria, Clostridia*, or *Lactobacilli*. In one embodiment, the bacteria are non-viable. In a preferred embodiment, the APC are dendritic cells (DC). In a further embodiment, the APC or the DC are autologous.

In specific embodiments of the subject invention, the administration of APC that have been pulsed with one or more bacteria and/or components of bacteria, for example, *Lactobacillus* strains such as *L. johnsonii*, can treat or prevent T1D in a subject. Specially exemplified herein is the use of LjN6.2. For example, vaccination with DC that have been pulsed with LjN6.2 or certain components of LjN6.2 conferred T1D resistance to DP rodents. Diabetes resistance in the DP rodents was correlated to a Th17 bias within the mesenteric lymph node (LN), which was associated with high levels of IL6 and IL23.

In one embodiment, the current invention provides a method of preparing a composition useful in treating or preventing T1D. The method comprises pulsing an APC with one or more bacteria, or components of one or more bacteria, wherein the bacteria, or the component of the bacteria, confer upon the APC the ability to inhibit the generation of diabetogenic T cells. The APC can be DC and the bacteria can be from the genera *Eubacterium, Clostridium,* or *Lactobacillus*. In one embodiment the bacterium is *Lactobacillus johnsonii* or LjN6.2. In another embodiment, the component of the bacteria is a membrane component.

In one embodiment, the APCs are pulsed with a bacterial component, or a composition that acts so as to confer upon the APCs the ability to inhibit generation of diabetes-promoting T-cells in a manner that is the same as, or analogous to, the effect had by bacteria on APCs. In a specific embodiment, APCs are contacted with a material that antagonizes the activity of suppressor of cytokine signaling-1 protein(s) (SOCS1).

The subject invention further provides methods to screen gut-derived bacterial strains (in vitro) for their ability to pulse APC and produce APC (immune system modulating compositions) as described herein. In one embodiment, the method of screening human gut-derived bacterium capable of inducing resistance to T1D comprises isolating human gut derived bacterium, pulsing human APC, for example, human DC, preferably, autologous DC, with the bacterium and/or components of bacterium, for example, bacterial lysates or bacterial membrane components, injecting the pulsed APC into humans, and identifying the bacterium that produced APC capable of reducing T1D onset in the humans.

| Description | Sequence | SEQ ID NO: |
|---|---|---|
| Forward primer for Actin amplification | 5'-CCT TCC TTC TTG GGT ATG CA-3' | 1 |
| Reverse primer for Actin amplification | 5'-GGA GGA GCA ATG ATC TTG AT-3' | 2 |

-continued

| Description | Sequence | SEQ ID NO: |
|---|---|---|
| Forward primer for Actin amplification in pancreas | 5'-CCA CAG CAC TGT AGG GTT TA-3' | 3 |
| Reverse primer for Actin amplification in pancreas | 5'-ATT GTC TTT CTT CTG CCG TTC TC-3' | 4 |
| Forward primer for CD3 amplification | 5'-GAC CTG ACA GCA GTA GCC AT-3' | 5 |
| Reverse primer for CD3 amplification | 5'-CTC CTT GTT TTG CCC TGT GG-3' | 6 |
| Forward primer for INFγ amplification | 5'-AAC TAT TTT AAC TCA AGT GGC AT-3' | 7 |
| Reverse primer for INFγ amplification | 5'-AGG TGT GAT TCA ATG ACG-3' | 8 |
| Forward primer for IL6 amplification | 5'-GGA AAT GAG AAA AGA GTT GTG C-3' | 9 |
| Reverse primer for IL6 amplification | 5'-CTC CAG AAG ACC AGA GGA AAT-3' | 10 |
| Forward primer for IL-23-p19 amplification | 5'-GCT CTC TCG GAA TCT CT-3' | 11 |
| Reverse primer for IL-23-p19 amplification | 5'-AAG CAG AAC TGG CTG TTG T-3' | 12 |
| Forward primer for IL-23R amplification | 5'-TGA AAG AGA CCC TAC ATC CCT TGA-3' | 13 |
| Reverse primer for IL-23R amplification | 5'-CAG AAA ATT GGA AGT TGG GAT ATG TT-3' | 14 |
| Forward primer for IL-17A amplification | 5'-ACT CTC CAC CGC AAT GA-3' | 15 |
| Reverse primer for IL-17A amplification | 5'-CTC TTC AGG ACC AGG AT-3' | 16 |
| Forward primer for ROR-γt amplification | 5'-ACA GCC ACT GCA TTC CCA GTT T-3' | 17 |
| Reverse primer for ROR-γt amplification | 5'-TCT CGG AAG GAC TTG CAG ACA T-3' | 18 |
| SOCS1-KIR | $^{53}$DTHFRTFRSHSDYRRI | 19 |
| SOCS1-KIR2A | $^{53}$DTHARTARSHSDYRRI | 20 |
| Tyrosine Kinase Inhibitory Peptide (TKIP) | WLVFFVIFYFFR | 21 |
| SOCS1-KIR dimer | DTHFRTFRSHSDYRRI_DTHFRTFRSHSDYRRI | 22 |
| JAK2 (1001-1013) | $^{1001}$LPQDKEYYKVKEP | 23 |
| pJAK2(1001-1013) | $^{1001}$LPQDKE$\underline{Y}$YKVKEP | 24 |

BRIEF DESCRIPTION OF THE FIGURES

To obtain a precise understanding of the current invention, a more particular description of the invention described herein will be rendered by reference to specific embodiments thereof that are illustrated in the appended Figures. Thus, understanding that these Figures depict only certain embodiments of the invention and are not therefore limiting in scope, the invention will be described and explained with additional specificity and detail through the use of the accompanying Figures.

This patent or application file contains at least one drawing executed in color. Copies of this patent or patent application publication, with color drawing(s), will be provided by the Office upon request and payment of the necessary fee.

FIG. 11. List of operational taxonomic units (OTU) at 97.5% sequence similarity with different relative abundances in NOD and NOR mice and OTU correlations with cytokine message. OTUs with at least 0.1% abundance in either NOD or NOR mice and are more abundant in either mouse type (p<0.05, indicated in parentheses) or correlated with Th17 associated factors are listed. Positive (+) and negative (−) correlations using Spearman correlation are indicated (significant correlations alpha<0.05).

DETAILED DESCRIPTION

Figure 1A:
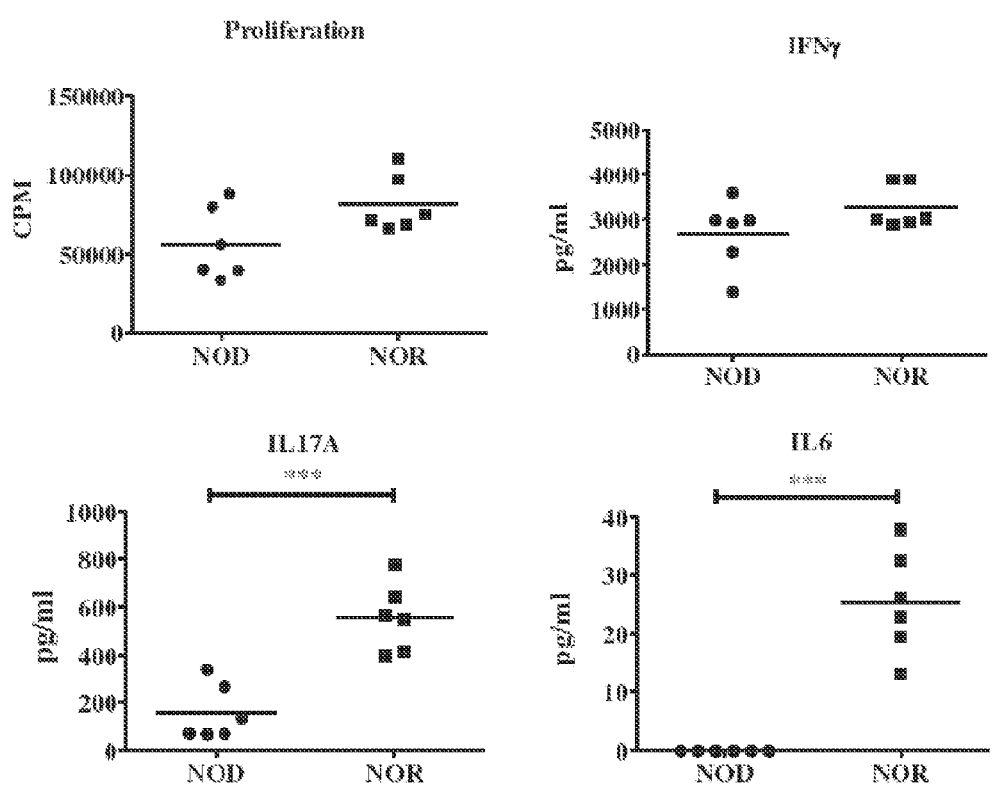
FIG. 1. Resistance to T1D in NOR mice, compared to NOD, is correlated to enhanced Th17 differentiation and APC. A. Whole LN cells, isolated from NOD and NOR mice, were pooled and stimulated with anti-CD3 antibody (anti-CD3). Forty-eight hours later, one half of the culture supernatant was collected from each sample and replenished with fresh media. At 72 hours each sample was pulsed with 3H thymidine, followed by assessment of proliferation by cellular incorporation of 3H thymidine 16 hours later. Collected supernatants were assessed for IFNγ, IL17A, and IL6 by ELISA as indicated. Each point within graphs shown indicates an individual mouse analyzed, with experiments performed in duplicate. B. Ex vivo LN cells, isolated from NOD and NOR mice, were pooled and stained with antibodies specific for T cell and APC markers followed by analysis by flow cytometry. Top: Graphs showing absolute numbers and relative frequency of $CD4^+$ and $CD8^+$ lymphocytes within pooled LN from NOD and NOR mice. Bottom: Graphs showing absolute number and relative frequency of total $CD11c^+$, $CD11b^+$, and $B220^+$ APC present within pooled LN cells from NOD and NOR mice. Absolute cell number counts for respective cell populations were obtained by multiplying gating frequencies obtained from flow cytometry with total cell numbers. Averages were based upon a minimum of 3 mice from each lineage =$p<0.01$, *=$p<0.005$.

The subject invention provides compositions for treating and/or preventing T1D and/or other autoimmune disorders. The compositions comprise one or more APC pulsed with one or more bacteria, or components of the bacteria, wherein the bacteria, or the components of the bacteria, confer upon the APC the ability to inhibit the generation of, for example, diabetogenic T-cells.

In one embodiment, the APC are autologous APC. Autologous APC refer to APC that are removed from a subject and later given back to the same subject. The composition can also include pharmaceutically acceptable carriers, additives, or excipients.

In preferred embodiments, the compositions comprise one or more DC that have been pulsed with one or more bacteria or components from the bacteria such that the pulsed DC, when administered to a diabetic subject or a subject at an increased risk for developing diabetes, inhibit the progression of diabetes. The bacteria used to pulse the DC are, preferably, those that confer upon the DC the ability to inhibit the generation of diabetogenic T-cells. In specific embodiments, these bacteria may be, for example, *Eubacteria* or *Clostridia*. In other embodiments, the bacteria may be *Lactobacilli*.

In accordance with the subject invention, it has been found that APC that have been pulsed with certain bacterial strains can be used to treat and/or prevent T1D and/or other autoimmune disorders. Accordingly, the subject invention also provides methods for preventing or treating autoimmune diseases. These methods comprise the administration of a composition of the subject invention, wherein the composition preferably comprises an effective amount of one or more pulsed APCs.

For the purpose of this invention, the term "treating or preventing" includes delaying the onset of the disease and/or reducing the severity or progression of the disease. A complete elimination of the disease is not required.

For the purposes of this invention, the term "pulsed APC" or "APC pulsed with compounds" refers to APC, for example DC, that have been exposed to one or more compounds, including but not limited to, purified peptides, bacterial isolates, bacterial culture lysates, bacterial membrane components, antagonists of SOCS1 protein, or other compounds that achieve an analogous effect on the APC. In certain embodiments, APC will present on their surfaces the antigens arising from peptides, bacterial isolates, bacterial culture lysates, or bacterial membrane components to which the APC were exposed. Also, when the pulsed APC interact with T-cells, a T-cell mediated immune response is induced against the antigens present on the APC surface. Accordingly, APC pulsed with one or more antigens can be used as vaccines against the one or more antigens.

In one embodiment, the APCs are pulsed with a bacterial component, or a composition that acts so as to confer upon the APCs the ability to inhibit generation of diabetogenic T-cells in a manner that is the same as, or analogous to, the effect had by bacteria on APCs. In a specific embodiment, APCs are contacted with a material that antagonizes the activity of suppressor of cytokine signaling-1 (SOCS1).

Administration of DCs that have been pulsed with LjN6.2 confer T1D resistance to DP rodents. Diabetes resistance in the DP rodents was correlated to a Th17 bias within the mesenteric LN, which was associated with high levels of IL6 and IL23.

Accordingly, the subject invention provides methods for treating or preventing T1D. These methods comprise administering to a subject having T1D or having an increased risk for developing T1D, a composition of the subject invention, wherein the composition comprises an effective amount of APC pulsed with one or more bacteria, or components of the bacteria, wherein the bacteria or the components of the bacteria confer upon the APC the ability to inhibit the generation of diabetogenic T cells.

The subjects that can be treated according to the method of the current invention include but are not limited to mammals. Non-limiting examples of mammal include cats, dogs, bovine, porcine, non-human primates and humans.

Specific embodiments of the subject invention provide administering to a subject DC that have been pulsed with *Lactobacillus* strains such as *L. johnsonii* to treat or prevent T1D in the subject.

Lymphocytes, isolated from NOD mice, possess a reduced Th17 bias when compared to counterparts from congenic, diabetes resistant NOR mice. This is notable since NOR and NOD mice contain significant numbers of potentially diabetogenic T lymphocytes, but only NOD mice proceed to T1D. The fact that congenic, diabetes resistant NOR mice possess a Th17 bias in comparison to NOD mice is comparable to a recent study showing that a Th17 bias is present within the subset of NOD mice naturally resistant to T1D (Kriegel et al. (2011)). Together these data suggest that in addition to the conversion of pre-diabetogenic T lymphocytes to either a Th2 lymphocyte or a Foxp3$^+$ regulatory T-cell phenotype, differentiation into the Th17 lineage may also inhibit the acquisition of diabetogenic effector functions.

In accordance with the subjection invention, diabetes inhibiting LjN6.2 enhanced APC maturation as denoted by induction of Th17 lymphocytes, up-regulation of MHCI, up-regulation of MHCII, increased IL6 production, and decreased surface expression of DEC205. Additionally, nonviable LjN6.2 was also found to be sufficient to mediate DC maturation, likely through an interaction between bacterial membrane components and DEC205.

Accordingly, the current invention further provides a method of preparing a vaccine useful in treating or preventing T1D, the method comprising pulsing an APC with a bacterium or a component of the bacterium, wherein the bacterium or the component of the bacterium confers upon the APC the ability to inhibit the generation of diabetogenic T-cells. The APC can be dendritic cells and the bacterium can be from the genera *Eubacterium, Clostridium,* or *Lactobacillus*. In one embodiment the bacterium is *L. johnsonii* or LjN6.2. In another embodiment, the component of the bacterium is a membrane component. In a further embodiment, the bacterium is nonviable.

The compositions of the subject invention can be prepared according to known methods for preparing pharmaceutically useful compositions. Non-limiting examples of formulations are described in a number of sources, which are well known and readily available to those skilled in the art. For example, *Remington's Pharmaceutical Science* (Martin E W [1995] Easton Pa., Mack Publishing Company, 19$^{th}$ ed.) describes certain formulations that can be used in connection with the subject invention. The formulations of the subject invention can include other agents conventional in the art having regard to the type of formulations described herein.

The amount of the therapeutic or pharmaceutical composition of the invention that is effective in the prevention and/or treatment of T1D can be determined by a person skilled in the art having the benefit of the current disclosure through standard clinical techniques. The precise dose to be employed in the formulation will also depend on several aspects, including but not limited to, the route of administration, the subject being treated, and the severity of the disease, and should be decided according to the judgment of the practitioner and each patient's circumstances. In one embodiment, effective doses can be extrapolated from dose-response curves derived from in vitro or animal model test systems.

The subject invention further provides methods to screen human gut-derived bacterial strains (in vitro) for their ability to be used in the DC compositions described herein. In one embodiment, human gut derived bacterial strains, that have been found to reduce T1D onset (using, for example, comparison techniques described in Brown et al. (2011), which is incorporated by reference herein in its entirety), can be incubated with human DC followed by assessing the ability of the gut flora modulated DC to inhibit the generation of diabetogenic T-cells. Of particular interest are the microbes identified in the U.S. Application Publication No. US-2012-0183513, which is incorporated by reference herein in its entirety.

The bacterial strain can be a mutant having substantially the same or improved properties of producing APC capable of treating or preventing T1D or it can be a naturally-occurring variant thereof. Procedures for making bacterial mutants are well known in the microbiological art and include, but are not limited to, exposure to ultraviolet light or nitrosoguanidine. Additional mutagenesis techniques are well known to a skilled artisan and such embodiments are within the purview of the current invention.

In another embodiment of the subject invention, the DCs can be pulsed with antigens or other cellular components rather than the intact cell. The antigen or other cellular component could be, for example, a cell surface molecule and would be chosen based upon the ability to confer upon the DCs the ability to treat and/or prevent T1D and/or other autoimmune disorders.

The subject invention further provides a method of preventing or treating T1D, the method comprising administering to a subject in need thereof, a composition comprising an effective amount of one or more pulsed DCs, optionally together with diet modifications, and/or the administration of other therapies, including, for example, immunosuppressants.

Other autoimmune conditions to which the treatments of the subject invention may be applied include, but are not limited to, rheumatoid arthritis, multiple sclerosis, thyroiditis, Crohn's disease, inflammatory bowel disease, Addison's disease, pancreas transplantation, kidney transplantation, islet transplantation, heart transplantation, lung transplantation, and liver transplantation.

Timing of Treatment

In one embodiment, the therapies of the subject invention can be used to treat and/or prevent T1D.

In one embodiment, treatment is administered prior to the onset of clinical manifestation of overt T1D. The time of administration is preferably before extensive irreversible beta cell destruction has occurred, as evidenced by, for example, the clinical onset of T1D.

As set forth in more detail below with respect to T1D, those skilled in the art, having the benefit of the instant disclosure can utilize diagnostic assays to assess the stage of disease progression in a patient and then administer treatment at the appropriate time as set forth herein.

With regard to the early detection of T1D, numerous autoantibodies have been detected that represent the onset of T1D. Also, new serologic markers associated with T1D continue to be described. Four islet autoantibodies appear to be the most useful markers of T1D: islet cell antibodies (ICA), insulin autoantibodies (IAA), glutamic acid decarboxylase autoantibodies (GADA), and insulinoma-associated-2 autoantibodies (IA-2A). These are discussed in more detail below; however, the use of these markers to identify those at an increased risk for developing T1D is well known to those skilled in the art. In a specific embodiment of the subject invention, treatment is administered when a patient has at least one antibody marker or, preferably, at least two of the antibody markers.

ICA serve an important role as serologic markers of beta-cell autoimmunity. Seventy percent or more of Caucasians are ICA-positive at onset of T1D. Following diagnosis, ICA frequency decreases, and fewer than 10% of patients still express ICA after 10 years. The general population frequency of ICA is between 0.1% and 0.3%. In a preferred embodiment of the subject invention, anti-T-cell globulin (ATG) is administered prior to a decrease in ICA.

IAA occur in 35-60% of children at onset of T1D but are less common in adults. For example, in Australians with new-onset T1D, IAA were present in 90% of children less than 5 years old, in 71% of children 5 to 10 year, and in 50% of children 10 to 15 year old. In Britons with T1D, IAA were identified in 83% of children less than 10 years old and in 56% of children older than 10 years old.

IAA have been detected in several other autoimmune diseases. IAA were identified in 15.9% of patients with Hashimoto's thyroiditis and 13.5% of Graves' disease subjects. In another study, IAA frequencies in various thyroid autoimmune diseases were 44% in Graves' disease, 21% in primary hypothyroidism, and 23% in chronic autoimmune thyroiditis, compared with 40% in primary adrenal failure, 36% in chronic hepatitis, 40% in pernicious anemia, 25% in rheumatoid arthritis, and 29% in systemic lupus erythematosus.

Approximately 2-3% of the general population express GAD autoantibodies. These antibodies are detected in 60% or more of new-onset cases of T1D. The frequencies of IA-2A and IA-2βA in general population are similar to GADA at 2-3%. IA-2A and IA-2βA are observed in 60% or more of new-onset T1D cases.

Early biochemical evidence of beta cell injury is a decreased first-phase insulin response to the administration of intravenous glucose (IVGTT). First-phase response is defined as the insulin concentrations at $^+1$ and $^+3$ min following completion of an intravenous bolus injection of glucose (e.g., 0.5 g/kg). There is also a dissociation in the beta cell response to secretagogues: initially the insulin response to intravenous amino acid administration (e.g., arginine) is preserved even while first-phase responses are deficient (Ganda et al., (1984)). In ICA-positive individuals eventually developing insulin-dependent diabetes, first-phase insulin release diminishes at a rate of about 20-40 µU/mL/year (Srikanta (1984)).

When beta cell mass has substantially declined to less than 50% but more than 10% of normal, the OGTT may display abnormalities such as impaired fasting glucose (110-125 mg/dL) or impaired glucose tolerance (2-h glucose post-75-g challenge: 140-199 mg/dL). An abnormal OGTT prior to the clinical onset of T1D is more likely observed in younger children. Clinical diabetes usually follows within 1-2 years of the onset of oral glucose intolerance. By the time acute symptoms of T1D develop, beta cell mass is believed to have declined by approximately 90% or more from baseline. In one embodiment of the subject invention, treatment is administered once oral glucose intolerance is observed.

Most current procedures for the prediction of T1D involve analyses of multiple islet autoantibodies. In every such study reported, nondiabetic individuals who express combinations of islet autoantibodies are found to be at an increased risk for T1D than individuals who express fewer varieties of islet autoantibodies. In addition, the total number of types of islet autoantibodies is usually more important than the specific combination of islet autoantibodies. In T1D subjects, islet autoantibodies can also reappear after pancreas or islet transplantation, predicting failure to become insulin-independent (Bosi (2001)).

Thus, in genetically predisposed individuals, an environmental trigger or triggers are believed to initiate beta cell autoimmunity, which can be identified by the presence of islet autoantibodies. With progressive beta cell damage, there is loss of first-phase insulin response to intravenous glucose administration. Subsequently the OGTT becomes abnormal, followed by symptoms of diabetes and the diagnosis of T1D. Clearly the detection of islet autoimmunity can therefore be used as a predictive marker for the subsequent development of T1D.

Both in non-diabetic relatives of T1D subjects and in the general population, the detection of islet autoantibodies identifies individuals who are at an increased risk to develop subsequent T1D (LaGasse et al. (2002)). Higher titers of ICA are more predictive than lower titers, and multiple islet autoantibodies are more powerful predictors than the presence of single autoantibodies. The combination of ICA plus low first-phase insulin secretion is possibly the strongest confirmed predictor of subsequent T1D as demonstrated in the DPT-1. When using single autoantibodies, comparative sensitivities for the prediction of T1D are as follows: ICA>GADA>IA-2A>>IAA. Combination islet autoantibody assays (e.g., the simultaneous detection of GADA and IA-2A (Sacks et al. (2001); Kawasaki et al. (2000)) will likely supersede ICA testing in future testing programs.

The majority of individuals with T1D have islet autoantibodies at the time of onset of the disease. In cases where it is difficult to differentiate type1 from type 2 diabetes, the presence of one or more islet autoantibodies (e.g., ICA, IAA, GADA, or IA-2A) is diagnostic of type 1a, immune-mediated diabetes (Rubinstein et al. (1981)). When individuals clinically present with a subtle, non-ketotic form of diabetes that may not be insulin-requiring yet are islet autoantibody-positive, LADA is diagnosed.

Administration and Formulation

The compositions are administered in a manner compatible with the dosage formulation, and in such amount as will be therapeutically effective. The quantity to be administered depends on the subject to be treated, including, e.g., the capacity of the individual's immune system to generate an immune response. Precise amounts of cells or active ingredient required to be administered depend on the judgment of the practitioner. However, suitable dosage ranges are of the order of a few thousand cells to millions of cells for cellular vaccines. For standard epitope or epitope delivery vaccines then the vaccine may be several hundred micrograms active ingredient per vaccination. Suitable regimes for initial administration and booster shots are also variable, but are typified by an initial administration followed by subsequent inoculations or other administrations.

The manner of application may vary widely; however, certain embodiments herein will be delivered intravenously, subcutaneously, peritoneally, intramuscularly, and vaginally or at the site of a tumor or infection. Regardless, any of the conventional methods for administration are applicable. The dosage will depend on the route of administration and will vary according to, for example, the type and weigh of the subject, severity of the disease, etc.

In many instances, it will be desirable to have multiple administrations of the composition, e.g., four to six administrations provided weekly or every other week. A normal vaccination regimen will often occur in two to twelve week intervals or from three to six week intervals. Periodic boosters at intervals of 1-5 years, usually three years, may be desirable to maintain protective levels of the immune response. The course of the immunization may be followed by assays for, e.g., T-cell activation, cytokine secretion or even antibody production, most commonly conducted in vitro. These immune response assays are well known to a person of ordinary skill in the art and such embodiments are within the purview of the current invention.

The compositions of the present invention may be provided in one or more "unit doses." Unit dose is defined as containing a predetermined-quantity of the therapeutic composition calculated to produce the desired responses upon administration to a subject, i.e., the appropriate route and treatment regimen. A quantity to be administered and a route of administration can be determined by a person of ordinary skill in the art. The subject to be treated may also be evaluated, in particular, the state of the subject's immune system and the protection desired. A unit dose need not be administered as a single injection but may include continuous infusion over a predetermined period of time. Unit dose of the present invention may be described in terms of mg of DNA/kg or protein/Kg of body weight, which can be about 0.05, 0.10, 0.15, 0.20, 0.25, 0.5, 1, 10, 50, 100, 1,000, or more.

Single or multiple administrations of the compositions are administered depending on the dosage and frequency as required and tolerated by a patient. In any event, the composition should provide a sufficient quantity of the active agent, for example pulsed APC, to effectively treat the subject. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Figure 15:
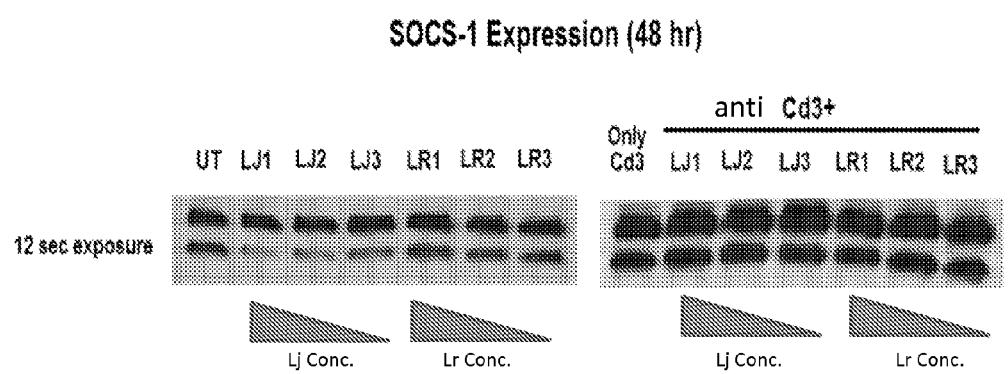
FIG. 15. *L. johnsonii*, but not *L. reuteri*, inhibits suppressor of cytokine signaling-1 (SOCS1) protein expression in a dose dependent manner in APC. Lymph nodes cells, isolated from non-diabetic NOD mice, were cultured with or without anti-CD3 in the presence or absence of graded doses of *L. johnsonii* or *L. reuteri*. After 48 hours cultured cells were lysed and lysates were subjected to electrophoresis followed by transfer to nitrocellulose. Western blot analysis of differences in suppressor of cytokine signaling-1 (SOCS1) in response to differential bacterial treatments is shown.

SOCS1 is present in numerous cell types, for example, immune cells, including APC and T-cells; other hematopoietic cells; and non-hematopoietic cells, for example, liver cells, pancreatic beta cells, etc. *L. Johnsonii* inhibits the ability of APC, for example DC, to mediate diabetogenic effector functions in T lymphocytes. *L. Johnsonii* inhibits SOCS1 levels in lymph node cells (FIG. 15). The SOCS family of proteins regulates immune cell functions by inhibiting responsiveness and/or production of various cytokines SOCS1 expression is believed to be modulated by the bacterial cell wall product, lipopolysaccharides (LPS).

In one embodiment, the current invention provides a correlation between the gut flora of a subject and the modulation of diabetogenic dendritic cell functions by the gut flora. Gut bacteria, particularly, can inhibit T1D initiation and progression by modulating the activities of APC, particularly, factors (e.g. LPS) from certain gut bacteria can confer upon the APC the ability to inhibit the generation of diabetogenic T cells.

The inhibitory effect of *L. Johnsonii* on SOCS1 level in the lymph node cells was not observed in presence of anti-CD3 (FIG. 15). Anti-CD3 is an activator of T cells and the inhibitory effect of *L. Johnsonii* on SOCS1 levels in the lymph node cells was not observed in the presence of anti-CD3. These data suggest that *L. johnsonii* mediated inhibition of SOCS1 occurs in non-T cells in the lymph node, namely, APC, particularly DC.

These data further suggest that modulation of SOCS1 signaling, for example, modulation through administration of an antagonist or a mimetic of SOCS1 can alter T1D onset. However, given the role of SOCS1 signaling in a number of cell types, directed regulation of SOCS1 signal is a preferred method, according to the subject invention, in preventing T1D compared to a generalized inhibition of SOCS1 signaling.

Accordingly, treatment of APC, for example autologous DC, with an antagonist of SOCS1 can be used according to the subject invention to produce APC capable of inhibiting the generation of pathological T-cells. APC treated with an SOCS1 antagonist can used to inhibit the generation of pathological T-cells to confer upon the APC the ability to inhibit the generation of pathological T-cells.

Accordingly, one embodiment of the current invention provides APC, for example, autologous DC, contacted with an antagonist of SOCS1, wherein upon administration to a subject, the APC inhibits the generation of diabetogenic T-cells in the subject.

In another embodiment, the current invention provides a method of treating or preventing T1D in a subject, the method comprising administering to the subject APC, for example, autologous DC, that have been treated/contacted with an antagonist of SOCS1, wherein the APC inhibits the generation of diabetogenic T-cells in the subject.

In a further embodiment, the current invention provides a method of producing an immune system modulating composition, the method comprising obtaining APC, for example, autologous DC, and treating/contacting the APC with an antagonist of SOCS1, wherein upon administration to a subject the APC inhibits the generation of pathological T-cells in a subject.

The antagonist of SOCS1 can be an agent that can inhibit activity and/or expression of SOCS1 protein or mRNA. The agent capable of inhibiting SOCS1 activity can be a small molecule compound, a mimetic (which can be a peptidomimetic), or a peptide. Examples of SOCS1 inhibitory peptides and/or mimetics are described in Waiboci et al. (2007a), Waiboci et al. (2007b), Ahmed et al. (2009), Ahmed et al. (2010), Larkin et al. (2013), and U.S. Pat. No. 7,189,694. Certain examples of peptides and mimetics capable of inhibiting SOCS1 activity are shown in Table 1. Additional examples of small molecule compounds, peptides, and mimetics that can inhibit the activity of SOCS1 are well known to a person of ordinary skill in the art and such embodiments are within the purview of the current invention.

TABLE 1

Examples of SOCS1 inhibitor mimetics and peptides.

| Peptide | Sequence |
|---|---|
| SOCS1-KIR | $^{53}$DTHFRTFRSHSDYRRI |
| SOCS1-KIR2A | $^{53}$DTHARTARSHSDYRRI |
| Tyrosine Kinase Inhibitory Peptide (TKIP) | WLVFFVIFYFFR |
| SOCS1-KIR dimer | DTHFRTFRSHSDYRRI_DTHFRTFRSHSDYRRI |
| JAK2 (1001-1013) | $^{1001}$LPQDKEYYKVKEP |
| pJAK2(1001-1013) | $^{1001}$LPQDKE$\underline{Y}$YKVKEP |

SOCS1-kinase inhibitory region (SOCS1-KIR) peptide, which include the kinase inhibitory region of SOCS1, and tyrosine kinase inhibitory peptide (TKIP), which is complementary to the auto-phosphorylation site of JAK2, inhibit signal transducers and activators of transcription 1 (STAT1) activation/phosphorylation. SOCS1-KIR and TKIP possess cell-penetrating capacity through the addition of a lipophilic palmitoyl-lysine group to the N terminal region of the peptide. SOCS1-KIR2A, possessing two alanine substitutions, has been used as a specificity control to SOCS1-KIR. SOCS1-KIR dimer consists of two SOCS1-KIR peptides separated by a spacer (indicated by "_"). JAK2(1001-1013) peptide is the region of the JAK2 protein shown to interact with the KIR of SOCS1. pJAK2 (1001-1013) is thought to be a more activated form of the peptide because the tyrosine residue (underlined) thought to be critical in the interaction between SOCS1 and JAK2 has been phosphorylated.

The agent capable of inhibiting the expression of SOCS1 expression can be a RNA, for example, siRNA, shRNA, or miRNA. Certain SOCS1 siRNA, shRNA, and miRNA are commercially available. Additional examples of SOCS1 inhibitory siRNA, shRNA, and miRNA are well known to a person of ordinary skill in the art or can be envisioned by a person of ordinary skill in the art and such embodiments are within the purview of the current invention.

One embodiment of the current invention provides compositions and methods for treating autoimmune diseases. The compositions of the current invention comprise APC, for example, DC, more particularly, autologous DC, pulsed with a bacterium or a component of the bacterium, wherein the bacterium or the component of the bacterium confers upon the APC the ability to inhibit the generation of T-cells promoting the development of the autoimmune disease in the subject.

Accordingly, the current invention also provides a method of treating an autoimmune disease in the subject, the method comprising administering to a subject having the autoimmune disease or having an increased risk of developing the autoimmune disease, a composition comprising an effective amount of an APC pulsed with a bacterium or a component of the bacterium, wherein the bacterium or the component of the bacterium confers upon the APC the ability to inhibit the generation of T-cells promoting the development of the autoimmune disease in the subject.

A further embodiment of the subject invention provides a method of preparing a vaccine to treat or prevent an autoimmune disease, the method comprising pulsing an APC with a bacterium or a component of the bacterium, wherein the bacterium or the component of the bacterium confers upon the APC the ability to inhibit the generation of T-cells promoting the development of the autoimmune disease in the subject.

Various autoimmune diseases that can be treated according to the compositions and methods of the current invention include, but are not limited to, acute disseminated encephalomyelitis (ADEM), Addison's disease, Alopecia areata, Amyloidosis, Autoimmune retinopathy, autoimmune thyroid disease, Axonal & neuronal neuropathies, chronic fatigue syndrome, chronic inflammatory demyelinating polyneuropathy (CIDP), Crohn's disease, Coxsackie myocarditis, dermatitis herpetiformis, experimental allergic encephalomyelitis, Evans syndrome, Fibromyalgia, Glomerulonephritis, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Kawasaki syndrome, Lupus (SLE), Lyme disease, chronic, Meniere's disease, Multiple sclerosis, Myasthenia gravis, Myositis, Narcolepsy, Neuromyelitis optica (Devic's), Neutropenia, Scleroderma, Sjogren's syndrome, Stiff person syndrome.

The subject invention further provides methods to screen bacterial strains from microflora in a subject (in vitro) for the ability to pulse APC and produce APC compositions against autoimmune diseases described herein. In one embodiment, the method of screening bacteria capable of inducing resistance to an autoimmune disease comprises isolating a bacterium from a subject, pulsing APC, for example, DC, preferably, autologous DC, with the bacterium and/or components of bacterium, for example, bacterial lysates or bacterial membrane components, injecting the pulsed APC into the subject, and identifying the bacterium that produce APC capable of reducing the onset of the autoimmune disease in the subject.

A further embodiment of the current invention provides APC, for example, autologous DC, contacted with an antagonist of SOCS1, wherein upon administration to a subject, the APC inhibits the generation of T-cells promoting the development of an autoimmune disease in the subject.

In another embodiment, the current invention provides a method of treating or preventing T1D in a subject, the method comprising administering to the subject APC, for example, autologous DC, that have been treated/contacted with an antagonist of SOCS1, wherein the APC inhibits the generation of T-cells promoting the development of the autoimmune disease in the subject. In a further embodiment, the current invention provides a method of producing a vaccine, the method comprising obtaining APC, for example, autologous DC, and treating/contacting the APC with an antagonist of SOCS1, wherein upon administration to a subject the APC inhibits the generation of T-cells promoting the development of the autoimmune disease in the subject.

The antagonist of SOCS1 described above in connection with the compositions and methods of treating or preventing T1D can also be used in the compositions and methods of the current invention to treat or prevent other autoimmune diseases.

The term "about" is used in this patent application to describe some quantitative aspects of the invention, for example, dose administered to a subject. It should be understood that absolute accuracy is not required with respect to those aspects for the invention to operate. When the term "about" is used to describe a quantitative aspect of the invention the relevant aspect may be varied by ±10% (e.g., ±1%, ±2%, ±3%, ±4%, ±5%, ±6%, ±7%, ±8%, ±9%, or ±10%).

Materials and Methods

Animals

Pre-diabetic NOD/ShiLtJ and age-matched NOR/LtJ mice (The Jackson laboratory, Bay Harbor, Me.) were maintained in specific pathogen-free conditions at the Association for Assessment and Accreditation for laboratory Animal Care (AAALAC) accredited University of Florida, under the supervision of Institutional Animal Care and Use Committee (IACUC). Pre-diabetes status of NOD/ShiLtJ mice was confirmed using a blood glucose monitoring unit (Lifescan One Touch) as having blood glucose levels below 250 mg/dl. Peripheral LN (axillary, inguinal, and brachial), mesenteric LN, pancreatic LN, pancreas, and spleens were extracted from each mouse for in vitro or ex vivo analysis. Prediabetic NOD/ShiLtJ and NOR/LtJ were euthanized followed by removal of peripheral LN (axillary, inguinal, and brachial), mesenteric LN, pancreatic LN, pancreas, and spleens for in vitro or ex vivo analysis.

Bone Marrow Derived DC Preparation

Bone marrow was removed from the femur and tibia bones of NOD mice and washed. Progenitor cells were subsequently incubated in RPMI 1640 supplemented with 10% fetal bovine serum, 1% anti-biotic/anti-mycotic, granulocyte/macrophage colony stimulating factor (GM-CSF) (20 ng/ml) in 24-well plates ($10^6$ cells/well). Old medium was removed and replaced with 1 ml fresh complete RPMI medium containing 20 ng/ml GM-CSF every 2 days. On day 8, aggregates were dislodged and transferred with complete RPMI medium into 100 mm petri dishes at a maximum of $10^7$ cells/dish. At 24 and 48 hour time points following transfer, non-adherent, non-proliferating, BMDC were collected from the dish and stored in a sterile flask.

Proliferation Assays

Lymphocyte proliferation assays were performed as previously described with modifications. $4 \times 10^5$ whole lymphocytes were incubated with 4 μg/mL anti-CD3 (clone 17A2; eBioscience, San Diego, Calif.) in supplemented RPMI 1640 (10-040-CV; Cellgro, Manassas, Va.) containing 10% fetal bovine serum (10082-147; Gibco, Carlsbad, Calif.), 1% anti-biotic/anti-mycotic (30-004CI; Cellgro) in 96-well round bottom plates. After 72 hours of incubation, cultures were pulsed with 0.5 mCi[$^3$H] thymidine. Thymidine incorporation was measured using a Beckman LS3801 Liquid Scintillation System.

In Vitro Cytokine Secretion Analysis

Whole lymphocytes or BMOC were incubated with 4 μg/mL anti-CD3, (LjN6.2) and/or *L. reuteri* TD1 (LrTD1) at various concentrations as indicated. At 48 hours, 100 μL of supernatant was removed from each well and replenished with fresh medium. Cytokine ELISAs were subsequently performed on harvested supernatants. ELISA kits were purchased from BD Bioscience: anti-IFNγ (555138; BD Biosciences, San Diego, Calif.), and anti-IL6 (555240). Capture mAb (555068) and detection mAb (555067) for IL17 were purchased from BD Biosciences. Cytokine standard for IL-17A was purchased from eBioscience (14-8171-80).

Flow Cytometry

Single cell suspensions of pooled LN (axillary, inguinal, brachial, mesenteric, and superficial cervical), and spleen were stained with the following mAbs for flow-cytometric analysis: anti-CD4-Pacific Blue (RM4-5), anti-MHC I-FitC (KH95), anti-CD11c-PE (N418; eBioscience, San Diego, Calif.), anti-B220-APC (RA3-6B2, eBioscience), anti-CD11b-A700 (M1/70), anti-CD11b-FitC (M1/70, eBioscience), anti-CD11e-FitC (N418, eBioscience), anti CD86-A700 (GL1), anti-CD80-PE (16-10A1), DEC 205-APC (205yekta) and anti-MHC II-FC (39-10-8) mAb. All flow cytometry antibodies were purchased from BD PharMingen unless otherwise stated. 50,000-100,000 live events were collected on a LSRII (BD PharMingen) and analyzed using FlowJo software (Tree Star, San Carlos, Calif.). The absolute numbers of cells recovered from various organs was determined by multiplying the total number of cells isolated from various tissues by the percentage of total cells bearing a lineage specific marker denoted by flow cytometry.

Pancreas RNA Isolation and Histology

Pancreases were harvested from NOD and NOR mice and snap frozen in OCT (Fisher, 14-373-65, Pittsburgh, Pa.) embedding medium in a dewer of liquid nitrogen and 2-methylbutane (Fisher, 03551-4). Blocks were sectioned on a Leica CM 1950 cryostat at a thickness of 40 microns. RNA was then isolated using the Arcturus PicoPure RNA Isolation Kit (Applied Biosystems, KIT0204, Carlsbad, Calif.). Purity of RNA was confirmed using a Nanodrop ND 1000 Spectrophotometer. Five micron sections were cut and stained with H&E. Photos were taken at 20× magnification using the Leica DM 2500 Microscope equipped with an Optronics color camera and MagnaFire software (Optronics, Goleta, Calif.).

RNA Isolation and RT-qPCR

Total RNA was extracted from the LN and spleens of NOD or NOR mice using the SV Total RNA Isolation System (Promega, Corp., Madison, Wis., USA), according to the manufacturer's recommended spin column extraction protocol. The concentrations and purity of the total RNA were determined using a SmartSpecPlus Spectrophotometer (BioRad, Hercules, Calif., USA). First-strand cDNA synthesis was performed using ImProm-II Reverse Transcription System (Promega, Corp., Madison, Wis., USA) or iScript RT Supermix for RT-qPCR (BioRad, 170-8841). Absolute QPCR SYBR Green Mix (ABgene Epsom, Surrey, UK) or iQ SYBR Green Supermix Sample (BioRad, 170-8880S) and gene specific primers (Table 2) al 200 nM were used to amplify relative amounts of cDNA on a PTC-200 Peltier Thermal Cycler with a CHROMO 4 Continuous Fluorescence Detector (BioRad). Amplification was performed and the fold-change in expression was calculated using the double 8CT method (i.e. using the equation T MCT) using BioRad software.

TABLE 2

Primers used in the RT-qPCR

| Primer | Sequence | SEQ ID NO: | Annealing Temperature (° C.) |
|---|---|---|---|
| Actin | F 5'-CCT TCC TTC TTG GGT ATG CA-3' | 25 | 55 |
|  | R 5'-GGA GGA GCA ATG ATC TTG AT-3' | 26 |  |
| Actin (Pancreas Only) | F 5'-CCA CAG CAC TGT AGG GTT TA-3' | 27 | 55 |
|  | R 5'-ATT GTC TTT CTT CTG CCG TTC TC-3' | 28 |  |
| CD3 | F 5'-GAC CTG ACA GCA GTA GCC AT-3' | 29 | 55 |
|  | R 5'-CTC CTT GTT TTG CCC TGT GG-3' | 30 |  |
| IFNg | F 5'-AAC TAT TTT AAC TCA AGT GGC AT-3' | 31 | 55 |
|  | R 5'-AGG TGT GAT TCA ATG ACG-3' | 32 |  |
| IL-6 | F 5'-GGA AAT GAG AAA AGA GTT GTG C-3' | 33 | 57 |
|  | R 5'-CTC CAG AAG ACC AGA GGA AAT-3' | 34 |  |
| IL-23p19 | F 5'-GCT CTC TCG GAA TCT CT-3' | 35 | 55 |
|  | R 5'-AAG CAG AAC TGG CTG TTG T-3' | 36 |  |
| IL-23R | F 5'-TGA AAG AGA CCC TAC ATC CCT TGA-3' | 37 | 55 |
|  | R 5'-CAG AAA ATT GGA AGT TGG GAT ATG TT-3' | 38 |  |
| IL-17A | F 5'-ACT CTC CAC CGC AAT GA-3' | 39 | 55 |
|  | R 5'-CTC TTC AGG ACC AGG AT-3' | 40 |  |
| RORgt | F 5'-ACA GCC ACT GCA TTC CCA GTT T-3' | 41 | 63 |
|  | R 5'-TCT CGG AAG GAC TTG CAG ACA T-3' | 42 |  |

Bacterial DNA Extraction and Analysis

Fresh stool samples were collected from NOD and NOR mouse strains and frozen at −80° C. Whole DNA was extracted from each stool sample using the Qiagen DNeasy Blood and Tissue kit following the manufacturer's instructions (Qiagen, Valencia, Calif., USA). Spectrophotometry was used to determine the DNA concentration and purity of each sample. Amplification and library construction of the V4 region of bacterial 16S rRNA genes was performed using the primers 515F and 806R with the addition of barcode sequences and required Illumina adapters. For the amplification, an initial denaturation step of 94° C. for 3 min, followed by 20 cycles of 94° C. for 45 sec, 50° C. for 30 sec, and 65° C. for 90 sec, and a final elongation step of 65° C. for 10 min was performed. PCR products were purified using the Qiagen™ PCR purification kit following the manufacturer's protocol (Qiagen, Valencia, Calif., USA).

Illumina Sequencing and Analysis 16S rRNA amplicon sequencing was performed using Illumina GAIIx sequencing platform (Illumina, Inc., CA, USA) generating 100×2 paired-end reads with an average of 60,409±17,336 reads per sample. The reads were clustered into OTU with 97.5% or greater similarity using USEARCH 6.0 and classified using an RDP database (RDP 10) modified by the TaxCollector program. Tables were created and filtered (50 reads for a given OTU in at least 3 samples; 96.6% of reads were retained) using Lederhosen. Bar graphs and statistical analyses were conducted in XLSTAT (version 2012.2.01; 2012 Addinsoft), an add-in to Microsoft Excel; (version 14.2.5; 2010 Microsoft Corporation, Redmond Wash.). Analyses included Spearman correlation on taxonomic (proportion of reads) and cytokine message data, PCA generation, Shannon diversity index calculation, and t-test of unequal variance to compare taxonomic abundance between NOD and NOR samples (performed using natural log-transformation of data; p-value≤0.05 was considered significant).

Mechanical Separation of Bacteria and Viability Assessment

Bacterial cells were incubated with 0.1 mm glass beads and homogenized through the use of a beadbeater (Qbiogene) according to manufacturers' instructions. Nonviable bacterial components were subsequently separated through ultra-centrifugation and labeled as membrane, which consisted of the pellet, and cytoplasmic, which contained the soluble fraction. Efficiency of bacterial disruption was assessed through the culture of bacterial lysates on agar plates under anaerobic conditions.

Statistical Calculations

Statistically significant differences were determined using Graph Pad Prism software using an unpaired, two-tailed student t-test unless otherwise indicated. Statistical significances are indicated with asterisks symbols: *p≤0.05;  p≤0.01; * p≤0.005.

Following are examples that illustrate procedures for practicing the invention. These examples should not be construed as limiting. All solvent mixture proportions are by volume unless otherwise noted.

Example 1—Diminished Peripheral Th17 Differentiation and APC Frequency is Correlated to T1D Onset In order to better understand the relationship between Th17 differentiation and T1D onset, IL17 production by stimulated NOD T lymphocytes was compared to that of NOR lymphocytes. Although proliferation and IFNγ production were comparable in activated NOD and NOR peripheral LN suspensions, three-fold more IL17 was produced by NOR lymphocytes (FIG. 1A). Since APC derived IL6 is required for Th17 differentiation, its production was measured in the NOD and NOR LN suspensions. Whereas no IL6 production was detected within NOD LN suspensions, IL6 production was readily observed within the activated NOR LN suspension (FIG. 1A). Together, these data show that in vitro activated LN suspensions from diabetes resistant NOR mice possessed higher levels of Th17 differentiation than pre-diabetic NOD counterparts.

Figure 1B:
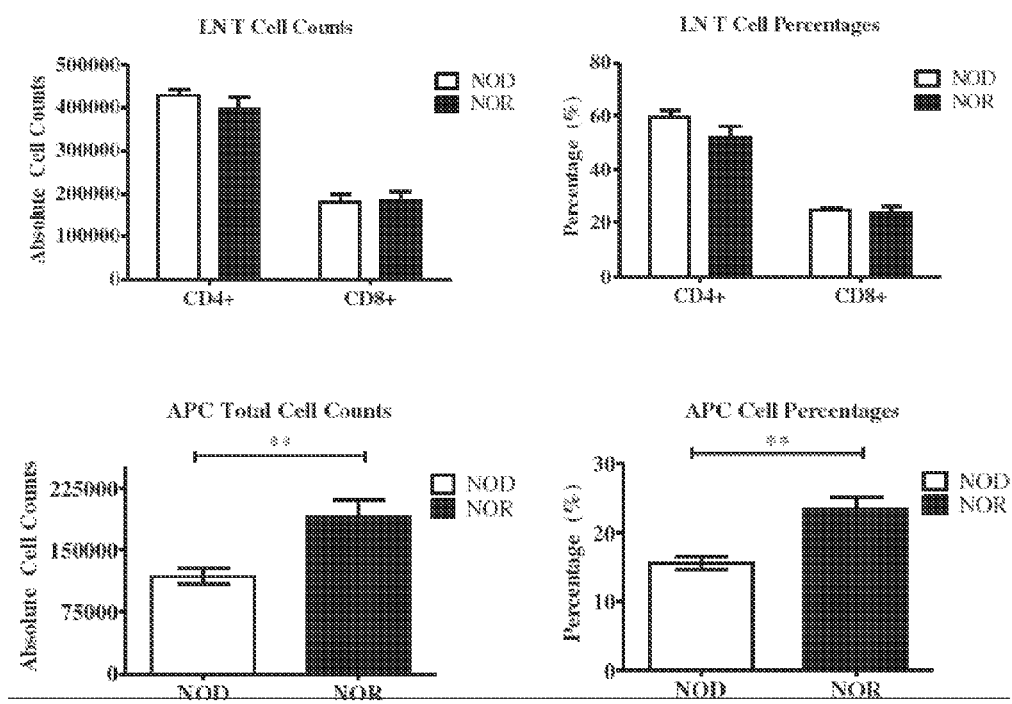
Figure 2A:
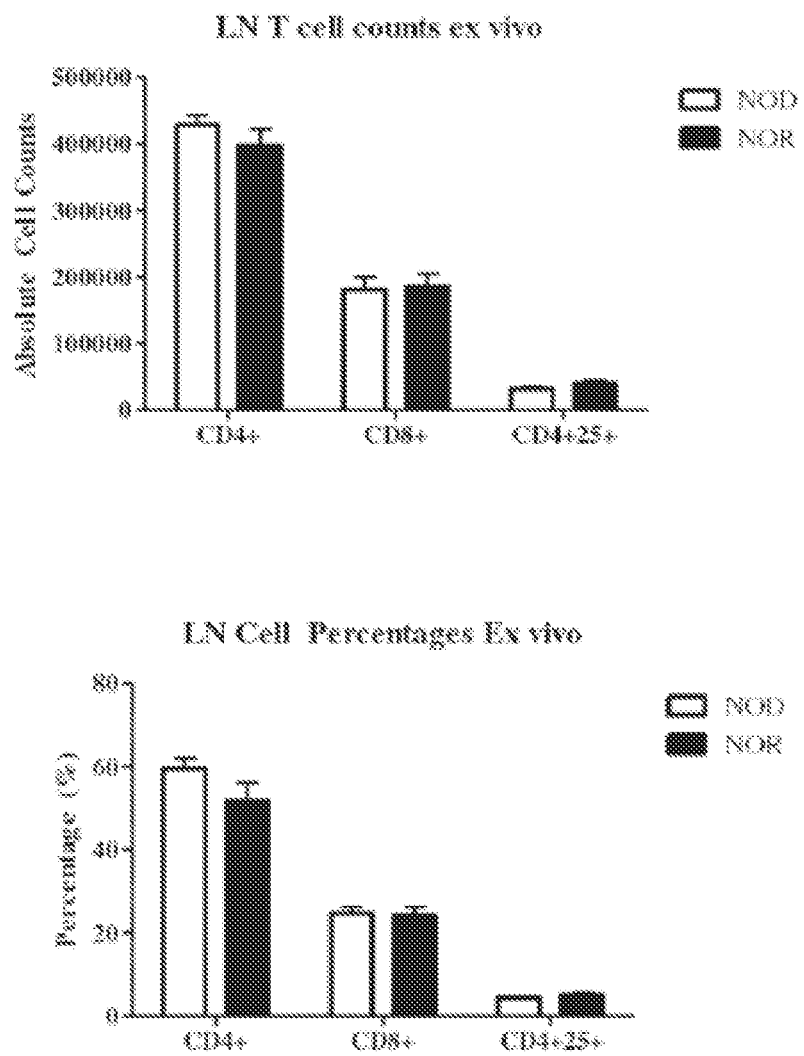
FIG. 2. IL17 deficiency is correlated to decreased APC, but not $CD4^+CD25^+$ regulatory T cells (Treg) numbers. Pooled leukocyte cells isolated from the axillary, brachial, mesenteric, inguinal, and cervical LN of NOD and NOR mice were labeled with T cell and APC specific antibodies ex vivo followed by flow cytometry analysis. A) Graphs showing the absolute number (top) and relative frequencies (bottom) of $CD8^+$, $CD4^+$, and $CD4^+CD25^+$ T lymphocytes present in the LN of NOD and NOR mice. B) Graphs showing the absolute number (top) and relative frequencies (bottom) of $B220^+$, $CD11b^+$, and $CD11c^+$ leukocytes present in the LN of NOD and NOR mice. Absolute cell number counts for $CD11b^+$, $CD11c^+$, and $B220^+$ populations were obtained by gating first for the CD3-population. =$p<0.01$, *=$p<0.005$. Data is averaged for 3 mice per set.

As differences in Th17 differentiation between NOD and NOR LN suspensions could be due to differences in leukocyte absolute numbers or frequencies, the cellular composition of the LN were analyzed. $CD4^+$ and $CD8^+$ T lymphocytes were found to be comparable in frequency and absolute number between NOD and NOR mice (FIG. 1B). Moreover, $CD4^+CD25^+$ regulatory T cells, which have been shown to play a critical role in the prevention of T1D onset, were also comparable in number and frequency between NOD and NOR peripheral LN (FIG. 2A). In stark contrast, NOD LNs possessed significantly fewer APC in both number and frequency (FIG. 1B).

Although deficiencies were observed among $CD11c^+$ DC and $CD11b^+$ macrophages, the most significant deficiencies were observed among the $B220^+$ B cells (FIG. 2B).

Together these data suggest that the reduced capacity of NOD mice to produce IL17, in comparison to NOR, may be due in part to reductions in APC function.

Example 2—Lymphocytes in Pancreas of NOD Mice Exhibit Reduced Th17 Bias Compared to Those from NOR Pancreas NOR and NOD mice experience leukocytic infiltrations of the pancreas; however, NOR mice are resistant to insulitis and T1D. Since reduced amounts of IL17 were observed in the peripheral LN of NOD mice compared to NOR, differences in Th17 associated factors within the leukocytic infiltrations of the pancreas were studied. Frozen-OCT embedded sections from the pancreases of both strains were generated, which were processed to either generate H&E stains or to measure the presence of Th17 related RNA. Sequential sections were utilized so that infiltrates shown in the H&E histology could be compared to RNA message levels.

Figure 3B:
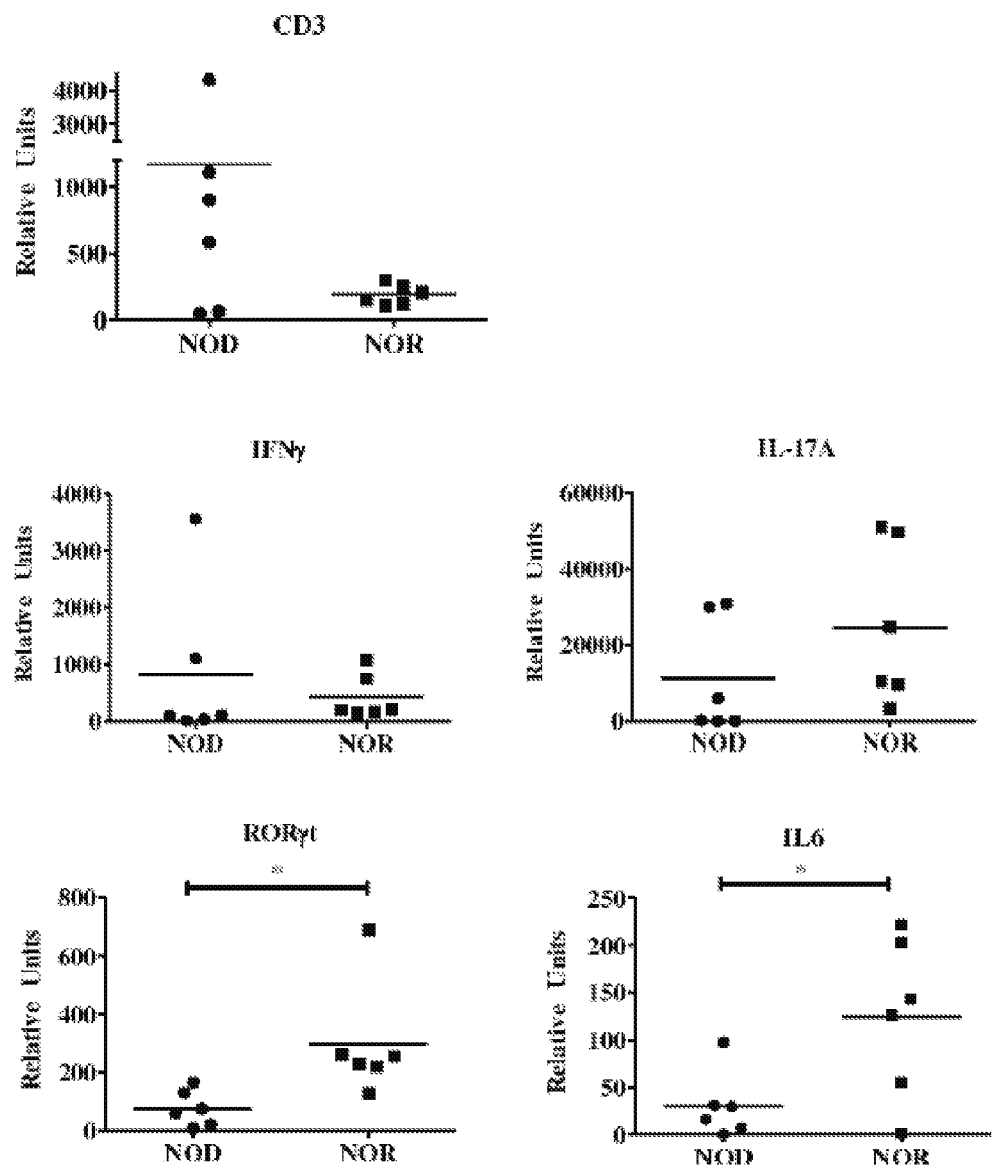
FIG. 3. Lymphocyte infiltrates present within the NOR pancreas display enhanced levels of Th17-related factors compared to NOD. Serial cryostat sections were obtained from the pancreases of 12 week old pre-diabetic NOD and NOR mice in order to analyze the location and phenotype of T lymphocytes infiltrates. A. H&E stains of pancreases isolated from 12 week old NOD and NOR mice. Photos are at 20× magnification and are representative of 3 mice from each category. Arrows indicate islets present in the pancreases of each mouse lineage. B. Graphs showing the relative expression of CD3, IFNγ, IL17A, RORγt, and IL6 RNA message in 40 micron cryostat sections isolated sequentially from H&E pancreas sections. Anti-CD3 results are shown relative to actin, while message levels are shown relative to anti-CD3. *=$p<0.05$. A total of 6 mice per category were examined in duplicate experiments.

Leukocytic infiltrations were observed in pancreatic H&E stains from both pre-diabetic 12 week old NOD and age-matched NOR mice (FIG. 3A). The NOD pancreas, however, possessed significantly more T lymphocyte infiltration and profound insulitis (as denoted by H&E (FIG. 3A) and CD3 message (FIG. 3B)).

Although IFNγ levels were indistinct, significantly higher levels of Th17 associated factors RORγt and IL6 were observed in the NOR pancreatic infiltrate compared to that of the NOD (FIG. 3B). IL17 message levels were consistently higher in the NOR compared to the NOD.

Together, these data show a reduced Th17 bias within the pancreatic infiltration of pre-diabetic NOD mice compared to NOR.

Figure 4A:
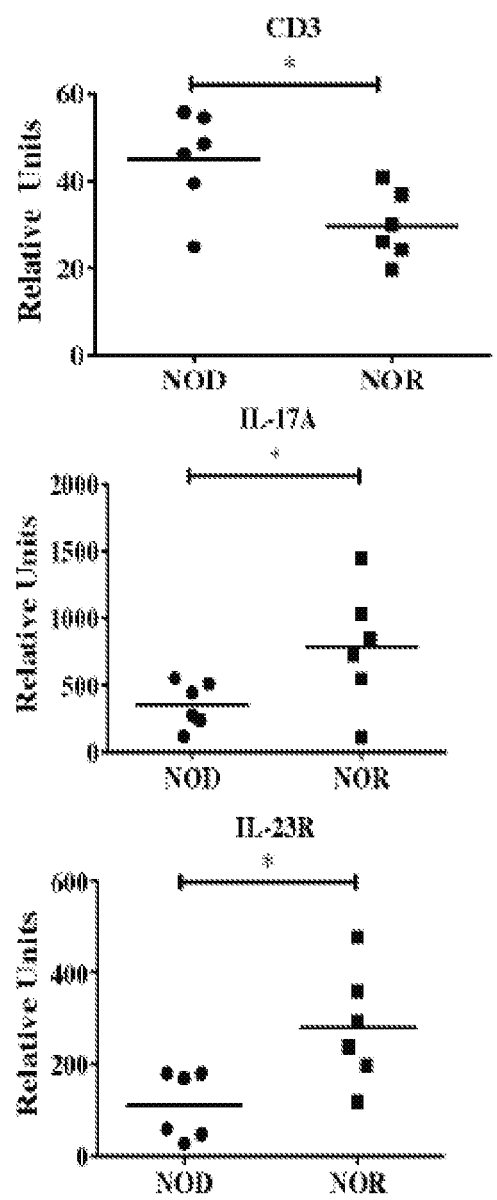
FIG. 4. NOD mice possess reduced Th17 bias and distinct bacterial flora composition in the mesentery LN compared to NOR mice. A. Graphs showing the expression of CD3, IL17A, and IL23R relative to β-actin in mesenteric LN isolated from 12 week old pre-diabetic NOD and NOR mice. Each point within graphs indicates an individual mouse analyzed, with experiments performed in duplicate. B. Top, PCA analysis of weighted distances between NOD and NOR mice evaluating microbial diversity. Each dot represents a sample and is identified based on type. Bottom, stacked bar graph showing the most abundant bacterial species present within stool samples isolated from NOD and NOR mice. The stacked bar graph depicts the genus of groups of bacteria sharing 97.5% sequence similarity with different abundances in NOD and NOR mice ($p<0.05$).
Figure 5:
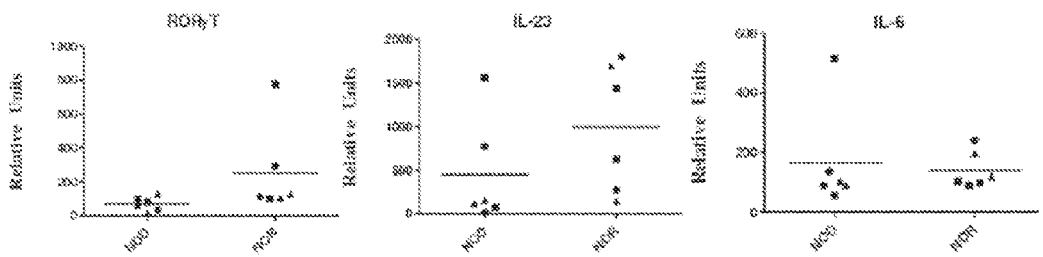
FIG. 5. Enhanced Th17 bias in NOR mesenteric LN is correlated to enhanced IL23 production. Graphs showing the expression of RoRyt, IL23, and IL6 relative to β-actin in mesenteric LN isolated from 12 week old pre-diabetic NOD and NOR mice. Each point within graphs indicates an individual mouse analyzed, with experiments performed in duplicate.

Example 3—NOD and NOR Mice Possess Distinct Th17 Biases in Mesenteric LN which is Correlated to Diverse Microbial Communities The mesenteric LN of NOR and NOD mice were examined for distinctions in cytokine profiles. Although mesenteric LN cells isolated from NOD mice possessed 50% more CD3 message, IL17 message levels were significantly lower in the NOD mesenteric LN (mLN) compared to the NOR. The Th17 specific transcription factor, RORγt, and surface protein, IL23 receptor (IL23R) were also consistently lower in the NOD mLN (FIG. 4A, 5). Notably, message levels for IL23 (required to sustain the Th17 phenotype), but not IL6 were consistently lower in the mLN of NOD mice compared to NOR (FIG. 5).

Figure 6:
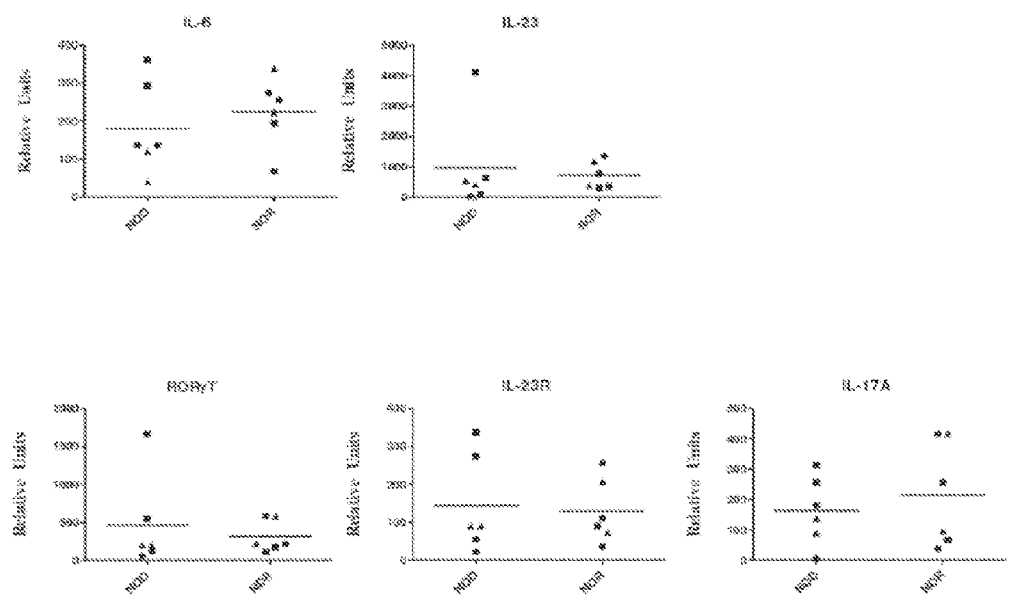
FIG. 6. Enhanced Th17 bias not observed in pancreatic LN. Graphs showing the expression of IL6, IL23, IL17A, and IL23R, and RORyt relative to CD3 in pancreatic LN isolated from 12 week old pre-diabetic NOD and NOR mice. Each point within graphs indicates an individual mouse analyzed, with experiments performed in duplicate.

Although lymphocytes present in the gut preferentially track to the pancreatic LN, distinctions in Th17 associated factors were not observed within the pancreatic LN (FIG. 6).

Together, these data show that pancreas and mLN of spontaneously diabetic NOD mice, possess a significantly lower fraction of T lymphocytes bearing aTh17 bias when compared to counterpart NOR mice.

Figure 4B:
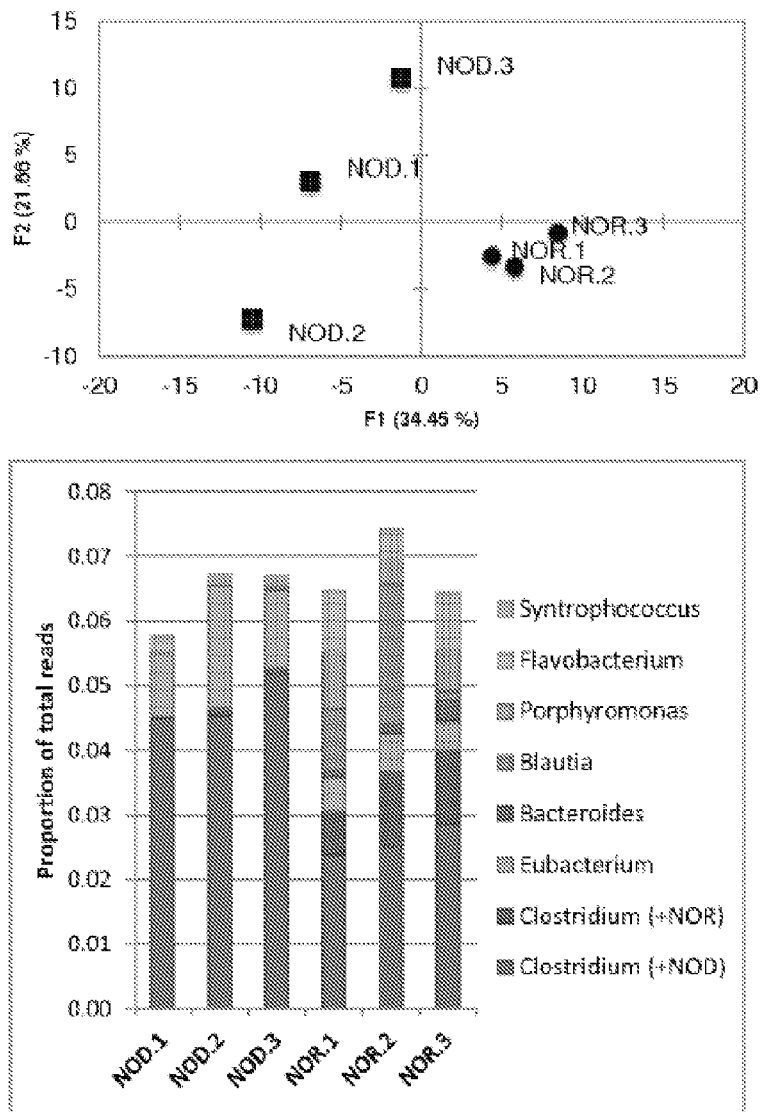

To analyze the bacterial communities present within NOD and NOR mice housed under the same conditions, barcoded 16S rRNA amplicon libraries were generated from stool samples obtained from the respective mice and sequenced with Illumina GAIIX. As depicted in FIG. 4B, PCA analysis revealed that the bacterial composition of NOR mice were more similar to other NOR mice than to communities obtained from NOD using 97.5% sequence similarity (depicted as weighted distances).

Figure 7A:
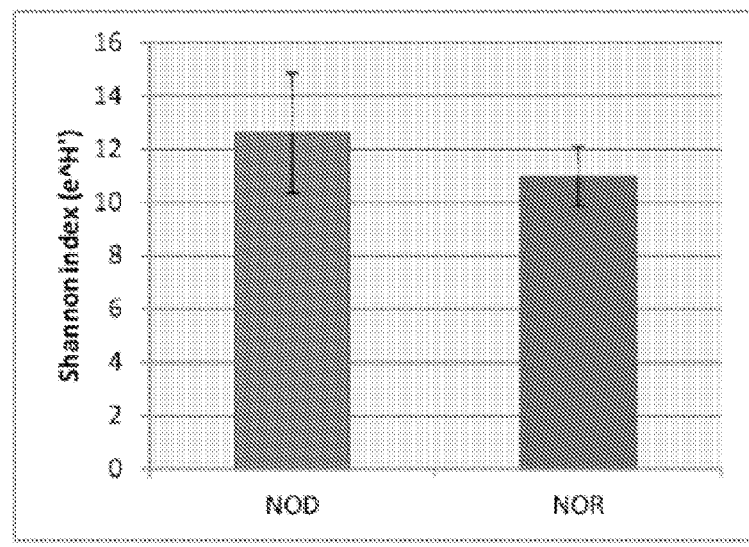
FIG. 7. Analysis of diversity and microbial communities in NOD and NOR mice at the phyla and genus levels. A) Bar graph showing no difference ($p=0.32$) in community diversity between NOD and NOR mice based on Shannon-Weaver diversity analysis. B) Stacked bar graphs showing the most abundant bacterial communities present with stools isolated from 8 week old pre-diabetic NOD and NOR mice at the genus and phyla level.
Figure 7B:
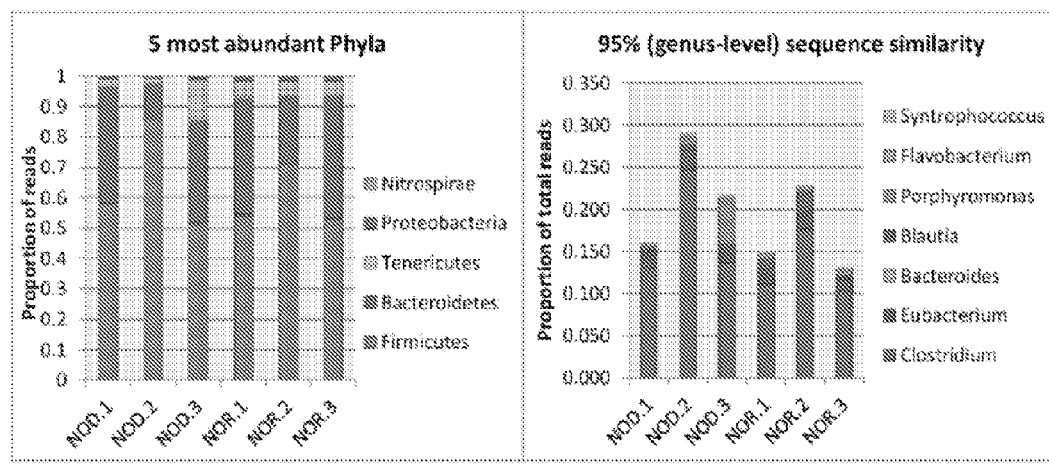

The Shannon diversity index detected no difference in overall community diversity between NOD and NOR mice, which was consistent with overall similarities observed at the phyla and genus levels (FIG. 7). However, 16S rRNA sequencing revealed that the abundance of specific strains present in the genera *Eubacterium, Clostridium, Syntrophococcus, Bacteroides*, and *Blautia* differed significantly from the bacterial communities observed in the stool samples of NOD and NOR mice (FIG. 4B and FIG. 11).

*Eubacterium* strains *E. dolichum* and *E. ventriosum* were observed in higher frequency in NOD mice, while *B. stercoris* was 2.5 fold higher (1.0% versus 0.4%) in NOR mice. Although *Clostridia* were present in both NOR and NOD mice, notably distinct species were present in each (denoted *Clostridia* ($^+$NOD) versus *Clostridia* ($^+$NOR), FIG. 4B and FIG. 11). Additionally, several OTU were found correlated with Th17 associated cytokine messages (FIG. 11).

Two *Clostridia* groups (one unidentified and another closely identifying to *Clostridium alkalicellulosi*) were negatively correlated with RORγt message and found in greater abundance in NOD mice, while *Clostridium septicum* was found to be positively correlated with IL23R message and more abundant in NOR mice. Specific *Eubacterium, Ruminococcus*, and *Ruminofilibacter* species were also correlated with Th17 factors.

Together these data suggest that the enhanced Th17 bias present within the pancreas and mesenteric LNs of diabetes resistant NOR mice, compared to NOD mice, was correlated to distinct microbial communities present within the gut.

Example 4—Defects in Th17 Phenotype can be Reversed Through APC Activation by LjN6.2

Figure 8A:
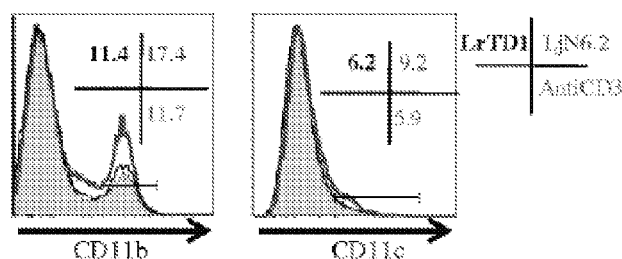
FIG. 8. LjN6.2, but not LrTD1, increases APC activation in NOD mice. Splenocytes derived from NOD or NOR mice, were cultured with graded doses of LjN6.2 or LrTD1 in the presence of anti-CD3. Following 48 hours incubation, samples were analyzed through flow cytometry for APC activation. A) Histograms showing changes in CD11b and CD11c frequencies upon treatment of NOD in vitro leukocyte cultures with LjN6.2 (red), LrTD1(black) or CD3 (shaded). B) Graphs showing percentage of $CD11b^+$ and $CD11c^+$ leukocytes in NOD and NOR cells cultures incubated with graded doses of bacteria as indicated. C) Graphs showing changes in MHC expression levels on $CD11c^+$ and $CD11b^+$ APC upon treatment with graded doses of LjN6.2 (shaded square) or LrTD1 (open square).
Figure 8B:
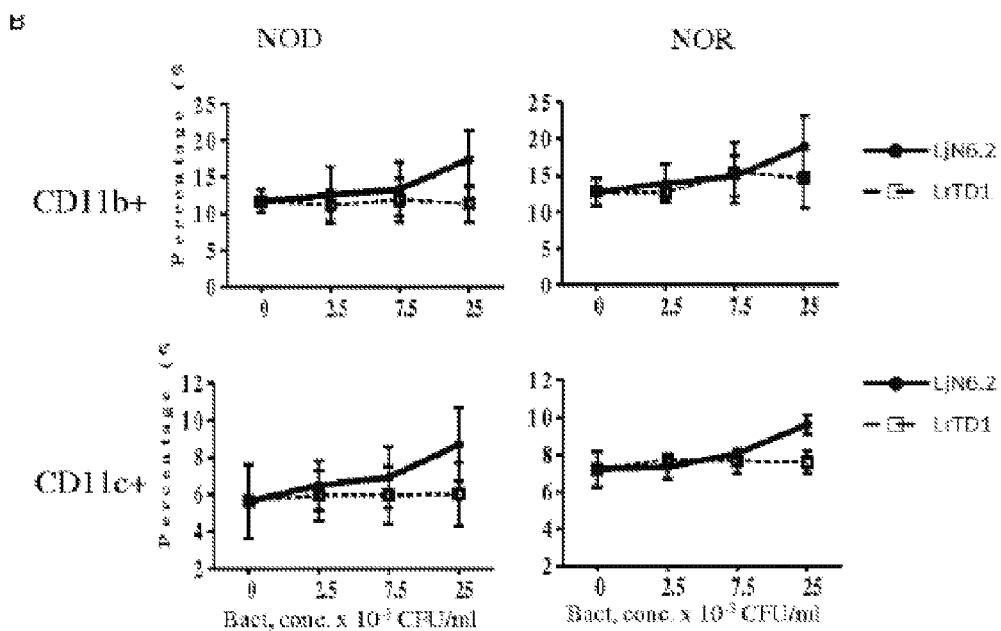

The oral transfer of a single strain of bacteria, LjN6.2, from diabetes resistant Bio-Breeding Diabetes Resistant (BBDR) rats to Bio-Breeding Diabetes Prone (BBDP) rats was sufficient to confer T1D resistance to BBDP rats (Valladares et al. (2010)). Moreover, the conferred T1D resistance was correlated to an APC dependent, Th17 bias observed in the BBDP rat and the NOD mouse (Lau et al. (2011)). Conversely, a second commensal bacterial strain, LrTD1, neither conferred T1D resistance nor mediated a Th17 bias (Valladares et al. (2010); Lau et al. (2011)). The capacity of LjN6.2 to modulate APC was compared to LrTD1 in vitro. Treatment of NOD derived primary cell cultures with LjN6.2, but not LrTD1, consistently up-regulated the frequency of both CD11b$^+$ and CD11c$^+$ leukocytes in a dose dependent manner (FIG. 8A, B). Although the frequencies of both CD11b$^+$ and CD11c$^+$ leukocytes present in NOD cultures increased in a dose dependent manner, CD11b$^+$ and CD11c$^+$ leukocytes in NOR cultures were only moderately increased (FIG. 4B).

Figure 8C:
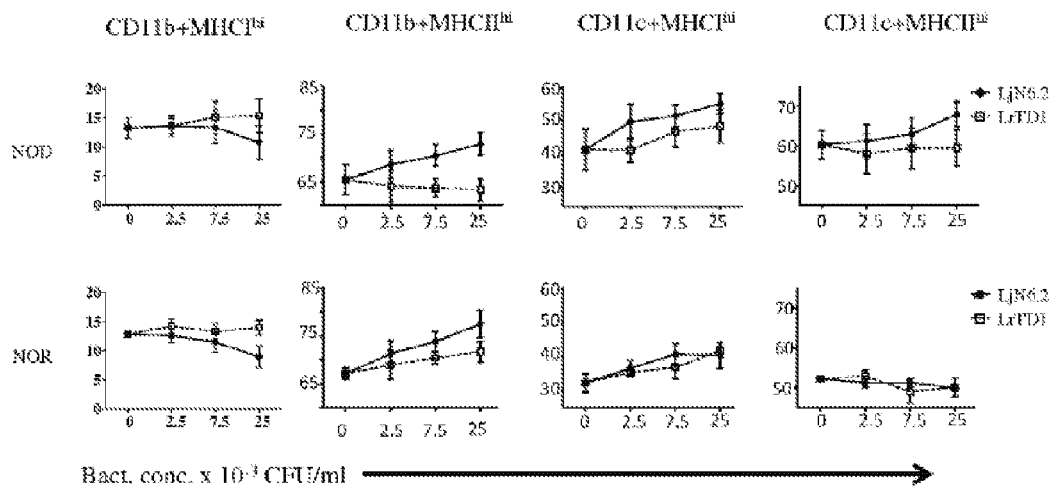

The capacity of LjN6.2 to modulate APC cell activation was examined. LjN6.2 treatment mediated a decrease in CD11b$^+$MHCIhi leukocytes and an increase in the frequency of CD11b$^+$MHCII$^{hi}$ leukocytes in both NOD and NOR cultures (FIG. 8C). Notably, although NOD derived CD11c$^+$ DC, treated with LjN6.2, upregulated levels of MHC classes I and II in a dose dependent manner, LjN6.2 failed to specifically increase MHCI and MHCII expression in NOR derived CD11c$^+$ DC (FIG. 8C). Significantly, in contrast to LjN6.2, LrTD1 treatment mediated reduced, or negligible, modulation of MHC (FIG. 8C).

Together these data show that LjN6.2, but not LrTD1, modulates the T cell priming capacity of NOD derived APC through increased frequency and up-regulation of MHC surface expression.

Example 5—LjN6.2 Decreases Endocytic Marker DEC205 on DC

Figure 9A:
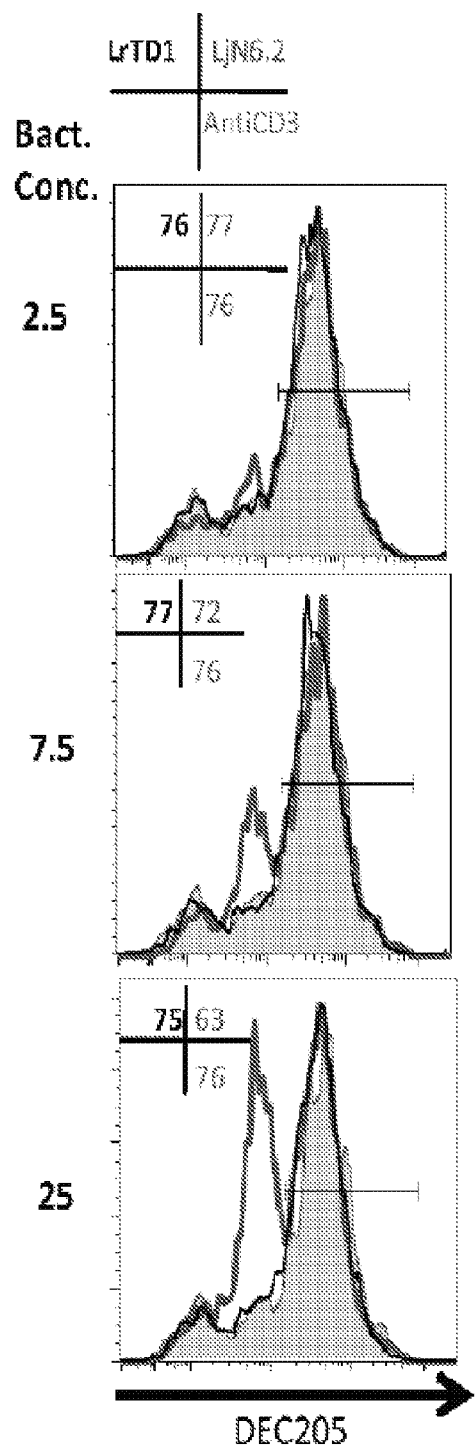
FIG. 9. Enhanced DC maturation mediated by LjN6.2 surface antigens. Splenocytes derived from NOD or NOR mice, were cultured with graded doses of LjN6.2 or LrTD1in the presence of anti-CD3, as in FIG. 4. Subsequent to incubation, samples were analyzed for expression of the endocytic marker, DEC 205. A) Overlay histograms showing changes in DEC205 frequency on $CD11c^+$ DC upon treatment of NOD cultures with varying doses of LjN6.2 and LrTD1. B) Graphical representations of DEC205 expression on $CD11c^+$ DC present within NOD and NOR cultures upon incubation with varying doses of LjN6.2 and LrTD1. C) Maturing DC (BMDC), derived from NOD mice were matured in the presence of GM-CSF, followed by incubation with LjN6.2 or beadbeater lysed LjN6.2 bacterial cellular components. Left, graph showing IL6 production by BMDC incubated with either intact LjN6.2, or fractional equivalents of nonviable lysed LjN6.2 components defined by ultracentrifugation as membrane (pellet components) or cytosolic (soluble) components. Right: photo showing anaerobic growth of LjN6.2 ($4\times10^5$) or fractional membrane equivalent on MRS media after 48 hours. Data shown is average of at least two independent experiments depicting at least 5 individual NOD and NOR mice.

The capacity of LjN6.2 and LrTD1 to modulate DEC205 levels on DC was measured. LjN6.2, but not LrTD1, mediated down-regulation of DEC205 expression in both NOD and NOR CD11c$^+$ DC in a dose dependent manner (FIG. 9). Notably, although LjN6.2 did not up regulate MHC molecules on NOR derived CD11c$^+$ leukocytes, it mediated DEC205 down modulation.

These data suggest that LjN6.2 interactions with DEC205 helped to mediate the capacity of DC to prime Th17 effector functions. LjN6.2 surface antigen modulates DC function.

Figure 9C:
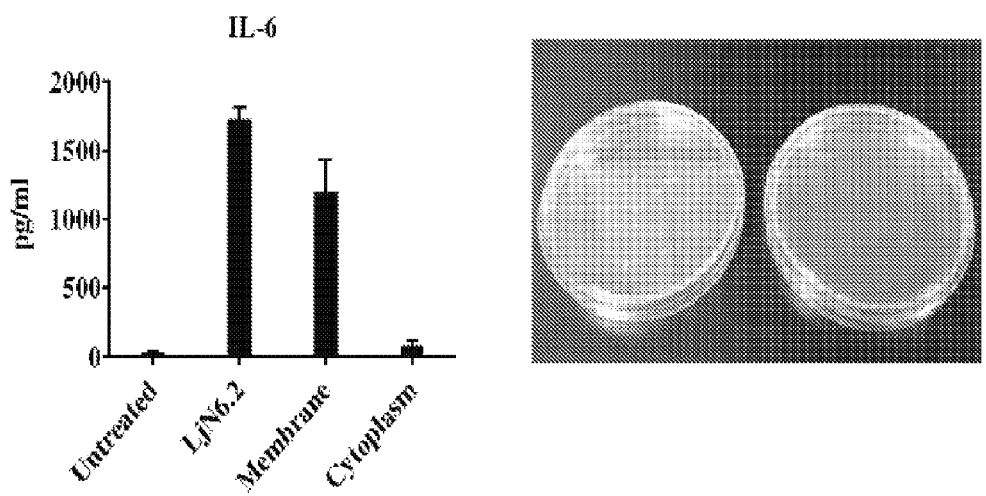
Figure 10:
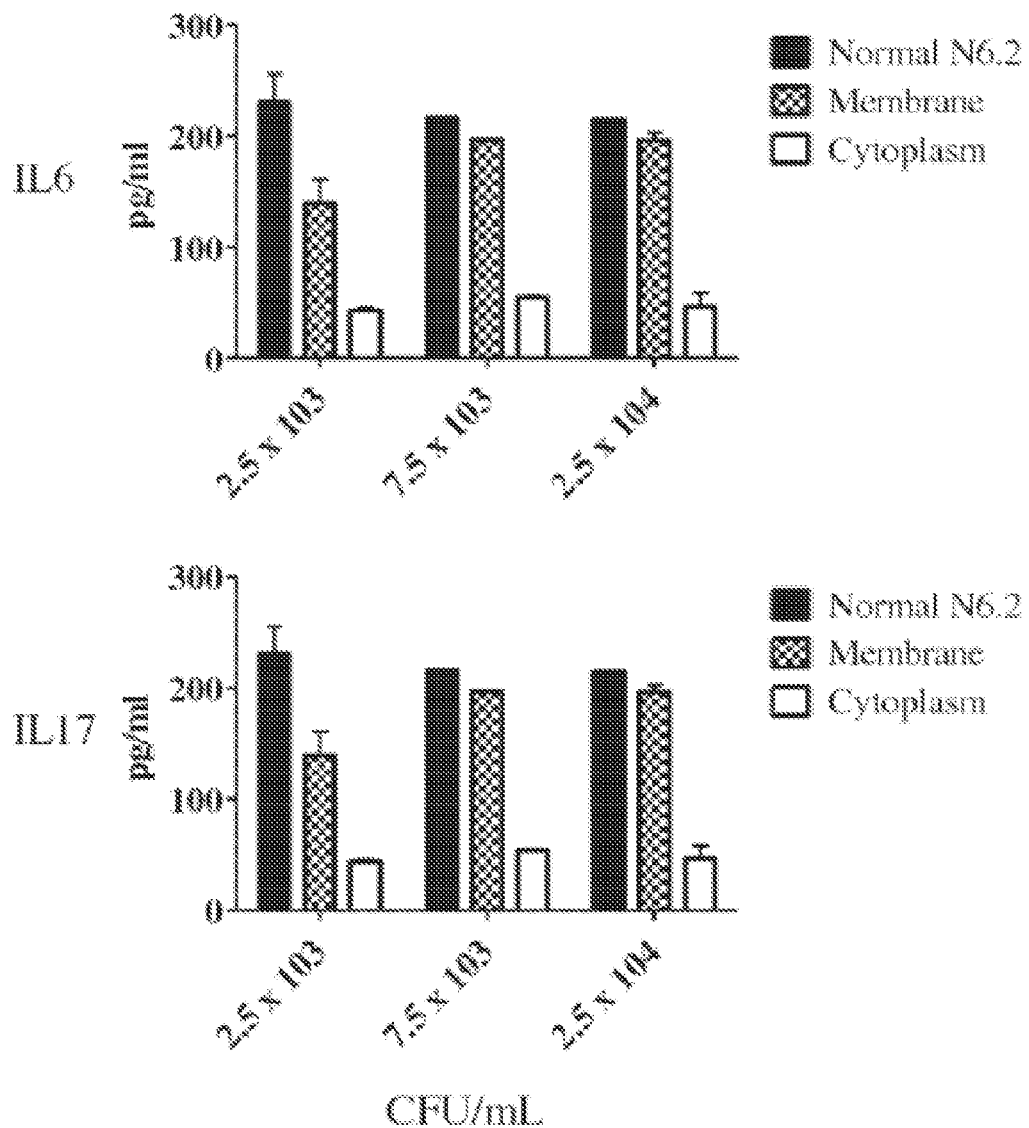
FIG. 10. Nonviable LjN6.2 surface components mediate enhanced DC maturation. Splenocytes ($4\times10^5$) were isolated from C57BL/6 mice and plated in the presence of anti-CD3 (4 µg/ml) and BMDC pulsed with either LjN6.2 or bacterial cellular equivalents of LjN6.2 membrane or cytosolic equivalents. Supernatants were removed at 48 hours for ELISA analysis. Graphs showing IL6 and IL17 production in response to varying concentrations of LjN6.2 or cellular equivalents of membrane components as indicated.

IL6 production by BMDC incubated with either viable LjN6.2, or bacterial cellular equivalents of bead beater ruptured LjN6.2 was measured. The bead beater ruptured LjN6.2 components were separated by centrifugation into insoluble (designated membrane) or soluble (designated cytoplasmic) components. BMDC incubated with LjN6.2 produced copious amounts of IL6 (FIG. 9C). Significantly, lysed LjN6.2 also mediated significant amounts of IL6 in a dose dependent manner (FIG. 9C and FIG. 10). In contrast, the cytoplasmic portion of the bacteria failed to up-regulate IL6 production. It is highly unlikely that the IL6 production is due to residual viable bacteria that survived the lysis process as no bacterial colonies developed in culture agar plates streaked with membrane components in contrast to plates streaked with LjN6.2 at the same initial bacterial concentration (FIG. 9C). It was also confirmed that IL6 and IL17 production could be mediated by LjN6.2 cell membrane components, but not the cytoplasmic components, in a dose dependent manner (FIG. 10).

Together, these data strongly suggest that components present on the surface of LjN6.2 specifically modulate the T cell priming capacity of DC, possibly through interactions with DEC205.

Figure 12:
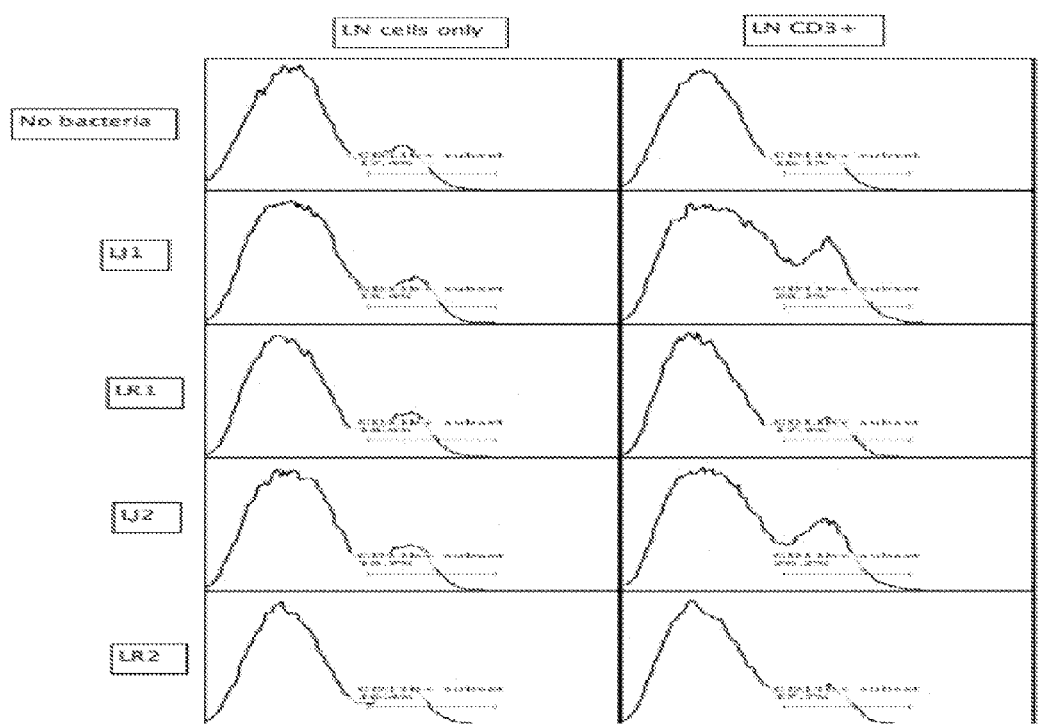
FIG. 12. LjN6.2 but not LrTD1 up-regulates expression of CD11b. LN cells (brachial, inguinal, cervical and mesenteric) were isolated from NOD mice and pooled, followed by culturing in the presence or absence of bacteria. After 48 hour incubation, supernatants were removed and cells were analyzed by flow cytometry. Please note that concentration 1 (Lj1 and Lr1) is 3 fold higher than concentration 2 (Lj2 and Lr2).
Figure 13:
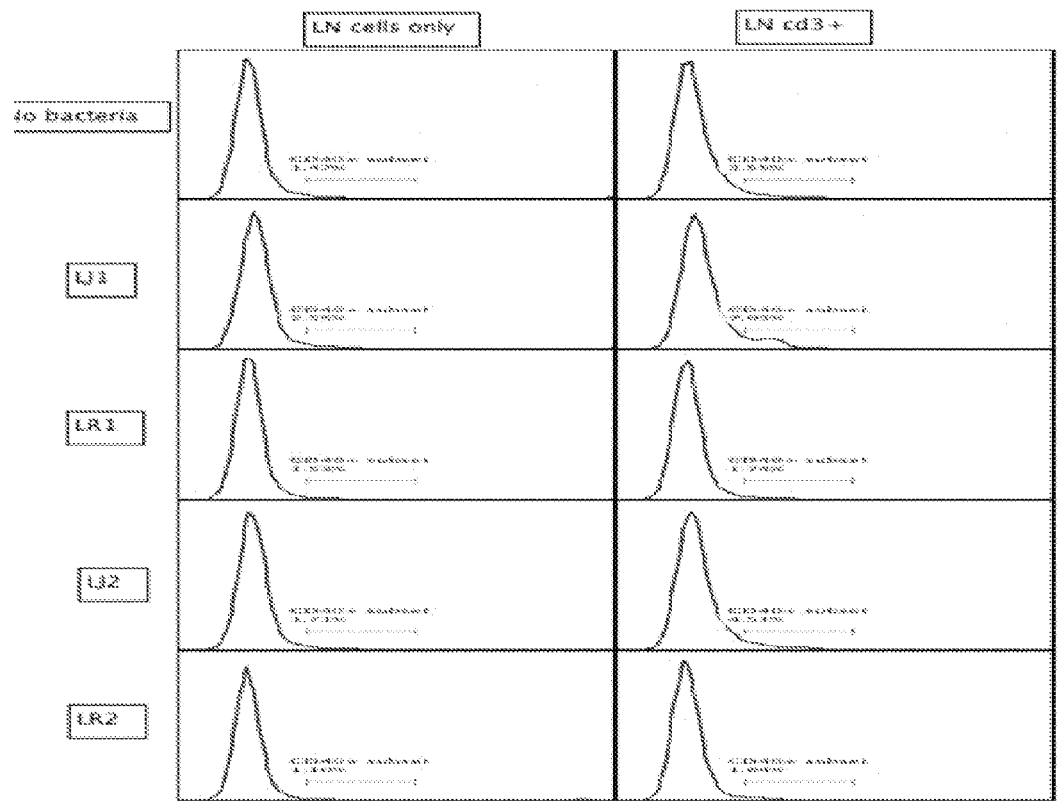
FIG. 13. LjN6.2 but not LrTD1 upregulated expression of MAC-1$^+$ CD40 cells. LN cells (brachial, inguinal, cervical and mesenteric) were isolated from NOD mice and pooled followed by culture in the presence or absence of bacteria. After 48 hour incubation, supernatants were removed and cells were analyzed by flow cytometry. CD11b$^+$ cells were first gated and then further analyzed for CD40 expression. Please note that concentration 1 (Lj1 and Lr1) is 3 fold higher than concentration 2 (Lj2 and Lr2).
Figure 14:
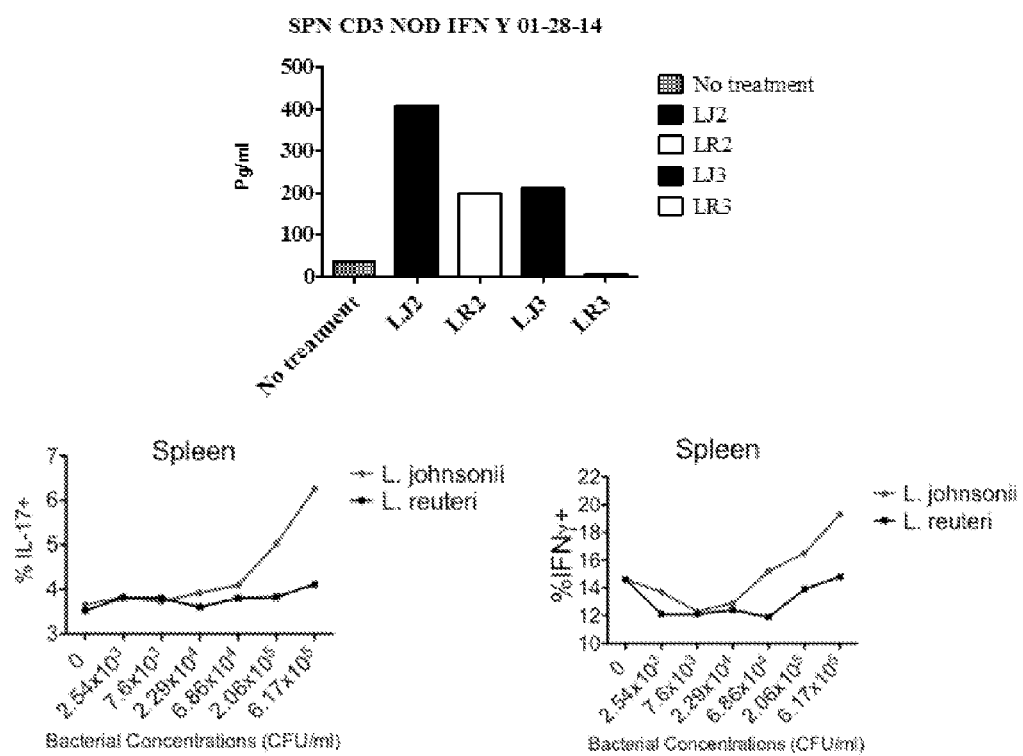
FIG. 14. *L. johnsonii* modulates adaptive immune response. *L. johnsonii* (but not *L. reuteri*) up-regulated CD40 expression on CD11b$^+$ leukocytes. *L. johnsonii* increased IFNγ production more profoundly than *L. reuteri*. Also, *L. johnsonii* increased the percentages of IFNγ$^+$ and IL17$^+$ T lymphocytes in a dose dependent manner.

Example 6—Gut-Flora-Modulated APC Influence Diabetogenic T Lymphocyte Effector Function in Rodents The rodent models of T1D were used to gain insight into the mechanisms by which gut-flora-modulated APC influence diabetogenic T lymphocyte effector function. FIG. 12 shows that *L. johnsonii*, but not *L. reuteri*, up-regulates CD11b. CD11b is the alpha chain of MAC-1, which is also known as complement receptor 3 when in association with CD18 (B2 integrin). MAC-1 is present on numerous cell types including macrophages, B cells and DC, which are APC. MAC-1 plays a critical role in regulation of inflammatory processes, cellular adhesions and signaling. Since it has been shown that CD40-CD40 ligand interactions promote MAC-1 expression, we analyzed CD40 expression. As seen in FIG. 13, *L. johnsonii* (but not *L. reuteri*) up-regulated CD40 expression on CD11b$^+$ leukocytes. To further test that gut flora/APC interactions can modulate diabetogenic T lymphocyte effector functions, we analyzed IL17 and IFNγ production. As can be seen in FIG. 14, *L. johnsonii* increased IFNγ production more profoundly than *L. reuteri*. We also found that *L. johnsonii* increased the percentages of IFNγ$^+$ and IL17$^+$ T lymphocytes in a dose dependent manner.

Example 7—LjN6.2 can Modulate Diabetogenic T Lymphocyte Effector Function in Human Immune Cells The goal of this study is to show that the immunomodulatory mechanisms through which different bacteria inhibit T1D in rodents and humans are similar. As such, one embodiment of the current invention provides seminal information regarding an immunological signature promoted by bacteria which provided bacteria mediated T1D resistance. This example of the current invention shows modulation of human APC by a bacterial strain shown to inhibit T1D in humans.

Peripheral blood mononuclear cells from human T1D patients and control subjects will be obtained and treated with *L. johnsonii* and *L. reuteri*. The supernatants will be analyzed by a sepsis array. A sepsis array can analyze 40 distinct proteins known to be generated by the immune system in response to bacterial interactions. Analysis of multiple proteins at once, using human samples is critical as the human samples are far scarcer than rodent samples.

Example 8—Gut Micro-Flora Mediated T1D Resistance

Beyond necessary TCR specificity, T cells must also acquire diabetogenic effector functions for T1D onset. Pre-diabetogenic T lymphocytes may be rescued from mediating T1D onset by acquiring IL4 production, or the Foxp3$^+$ regulatory T cell phenotype. Notably, acquisition of the Th17 effector function is also correlated to T1D resistance in the NOD mouse. The current invention shows that lymphocytes, isolated from NOD mice, possess a reduced Th17 bias when compared to counterparts from congenic, diabetes resistant NOR mice. This is notable since NOR and NOD mice contain significant numbers of potentially diabetogenic T lymphocytes, but only NOD mice proceed to T1D. The fact that congenic, diabetes resistant, NOR mice possess a Th17 bias in comparison to NOD mice is comparable to a recent study showing that a Th17 bias is present within the subset of NOD mice naturally resistant to T1D. Together these data suggest that in addition to the conversion of pre-diabetogenic T lymphocytes to either a Th2 lymphocyte or a Foxp3$^+$ regulatory T cell phenotype, differentiation into the Th17 lineage may also inhibit the acquisition of diabetogenic effector functions.

A peaceful mutualism exists between resident gut bacteria and the mammals in which they reside: the host provides food for the commensal bacteria, which in turn provide nutrients to the host by metabolizing otherwise indigestible food. In addition, a dynamic equilibrium also exists between resident gut flora and the development of the mammalian immune system. In particular, Th17 effector functions are induced by resident commensal bacteria, and subsequently regulate the composition of bacteria residing within the gut. Strikingly, numerous studies have shown that modulation of gut composition can alter onset of T1D. Moreover, it has been recently demonstrated that distinct, naturally occurring microbial communities reside within the gut of diabetes prone and resistant rats, and within the subset of female NOD mice naturally resistant to T1D compared to susceptible syngeneic mice. Significantly, LjN6.2, isolated from BBDR rats, and SFB, identified in T1D resistant NOD mice, have been correlated with both T1D resistance and mediating a Th17 bias. The current invention shows that congenic, diabetes resistant, NOR mice possess a Th17 bias, in comparison with NOD mice, and also possess distinct microbial communities. It is interesting that certain *Clostridial* strains preferentially segregated with NOD and NOR mice, as specific *Clostridial* strains have been shown to modulate T lymphocyte effector functions by inducing regulatory T cells. A recent study revealed that patients with T1D related autoimmune onset had bacterial communities that were very distinct from their first degree relatives. Notably, distinctions in the genus *Eubacteria* were observed between T1D patients and matched controls, diabetes prone and resistant rats, and in our current study between NOD and NOR mice. Together these studies suggest that gut flora composition is an environmental factor intimately involved in the onset of autoimmune T1D. Furthermore, these data suggest that alteration of T lymphocyte effector functions, in response to specific bacteria, may inhibit their acquisition of diabetogenic effector functions.

APC, in particular DC, maintain immune homeostasis by providing signals sufficient to activate pathogen-specific naïve T lymphocytes while being able to induce tolerance in naïve T cells specific to self-tissues and commensal bacteria. APC modulate immune responses by providing antigen presentation, necessary co-stimulatory signals, and appropriate cytokine environment. Notably, repair of defective APC priming, sufficient to inhibit T1D onset in rodent models, can be accomplished by immuno-stimulation.

In apparent contrast, T1D onset can also be inhibited through the generation of Foxp3$^+$ regulatory T cells which can be mediated by tolerogenic, immature DC. However, despite the contrast, it is clear that DC possess the capacity to modulate the effector functions of T lymphocytes, making it very likely that DC maturation can be skewed away from a diabetogenic T cell promoting phenotype. The current invention shows that diabetes inhibiting LjN6.2 enhanced APC maturation as denoted by induction of Th17 lymphocytes, down-regulation of MHCI, up-regulation of MHCII, increased IL6 production, and decreased surface expression of DEC205. Additionally, the current invention shows that nonviable LjN6.2 was sufficient to mediate DC maturation, likely through an interaction between bacterial membrane components and DEC205. Oral feeding of LjN6.2, or the administration of an LjN6.2-pulsed DC vaccination into the footpad of NOD mice, was sufficient to mediate a systemic Th17 bias. Therefore, restoration of DC function by oral administration of specific bacteria, or administration of a vaccine composed of gut flora modified DC, can be used to restore immune tolerance.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Ahmed C. M., Dabelic R., Waiboci L. W., Jager L. D., Heron L. L., and Johnson H. M. 2009. SOCS1 mimetics protect mice against lethal Poxvirus infection: identification of a novel endogenous antiviral system, *J. of Virol.*, 83, 3:1402-1415.
2. Ahmed C. M., Dabelic R., Martin J. P., Jager L. D., Mohammad S. H., and Howard J. M. 2010. Enhancement of antiviral immunity by small molecule antagonist of suppressor of cytokine signaling. *J. of Immunol.* 185: 1103-1113.
3. Atarashi, K., T. Tanoue, T. Shima, A. Imaoka, T. Kuwahara, Y. Momose, G. Cheng, S. Yamasaki, T. Saito, Y. Ohba, T. Taniguchi, K. Takeda, S. Hori, I. I. Ivanov, Y. Umesaki, K. Itoh, and K. Honda. 2011. Induction of colonic regulatory T cells by indigenous *Clostridium* species. Science 331: 337-341.
4. Atkinson, M. A. and A. Chervonsky. 2012. Does the gut microbiota have a role in T1D? Early evidence from humans and animal models of the disease. *Diabetologia* 55: 2868-2877.
5. Belkaid, Y. and G. Oldenhove. 2008. Tuning microenvironments: induction of regulatory T cells by DC. Immunity 29: 362-371.
6. Bending, D., H. De La Pena, M. Veldhoen, J. M. Phillips, C. Uyttenhove, B. Stockinger, and A. Cooke. 2009. Highly purified Th17 cells from BDC2.5NOD mice convert into Th1-like cells in NOD/SCID recipient mice. *J. Clin. Invest.*
7. Bettelli, E., Y. Carrier, W. Gao, T. Korn, T. B. Strom, M. Oukka, H. L. Weiner, and V. K. Kuchroo. 2006. Reciprocal developmental pathways for the generation of pathogenic effector TH17 and regulatory T cells. *Nature* 441: 235-238. 88.
8. Bosi, E. et al. 2001. Diabetes 50:2464-2471.
9. Brown, C. T., A. G. Davis-Richardson, A. Giongo, K. A. Gano, D. B. Crabb, N. Mukherjee, G. Casella, J. C. Drew, J. Ilonen, M. Knip, H. Hyoty, R. Veijola, T. Simell, O. Simell, J. Neu, C. H. Wasserfall, D. Schatz, M. A. Atkinson, and E. W. Triplett. 2011. Gut microbiome metagenomics analysis suggests a functional model for the development of autoimmunity for T1D. PLoS One 6: e25792.
10. Brugman S, Klatter F A, Visser J T J, Wildeboer-Veloo A C M, Harmsen H J M, Rozing J, Bos N A. (2006) Antibiotic treatment partially protects against type 1 diabetes in the Bio-Breeding diabetes-prone rat. Is the gut flora involved in the development of type 1 diabetes? Diabetologia 49: 2105-2108.
11. Butler, M., A. S. Morel, W. J. Jordan, E. Eren, S. Hue, R. E. Shrimpton, and M. A. Ritter. 2007. Altered expression and endocytic function of CD205 in human DC, and detection of a CD205-DCL-1 fusion protein upon DC maturation. *Immunology* 120: 362-371.
12. Calcinaro F, Dionisi S, Marinaro M, Candeloro P, Bonato V, Marzotti S, Corneli R B, Ferretti E, Gulino A, Grasso F, De Simone C, Di Mario U, Falorni A, Boirivant M, Dotta F. (2005) Oral probiotic administration induces interleukin-10 production and prevents spontaneous autoimmune diabetes in the non-obese diabetic mouse. Diabetologia 48: 1565-1575.
13. Campbell, I. L., L. Oxbrow, and L. C. Harrison. 1991. Reduction in insulitis following administration of IFN-gamma and TNF-alpha in the NOD mouse. J. Autoimmun. 4: 249-262.
14. Curtis M M & Way S S (2009) Interleukin-17 in host defence against bacterial, mycobacterial and fungal pathogens. Immunology 126: 177-185.
15. Fisher, 14-373-65, Pittsburgh, Pa.
16. Fukaya, T., R. Murakami, H. Takagi, K. Sato, Y. Sato, H. Otsuka, M. Ohno, A. Hijikata, O. Ohara, M. Hikida, B. Malissen, and K. Sato. 2012. Conditional ablation of CD205$^+$ conventional DC impacts the regulation of T-cell immunity and homeostasis in vivo. *Proc. Natl. Acad. Sci. U.S.A* 109: 11288-11293.
17. Ganda, O. P. et al., 1984. "Differential sensitivity to beta-cell secretagogues in early, type 1 diabetes mellitus," *Diabetes* 33: 516-521.
18. Giongo, A., K. A. Gano, D. B. Crabb, N. Mukherjee, L. L. Novelo, G. Casella, J. C. Drew, J. Ilonen, M. Knip, H. Hyoty, R. Veijola, T. Simell, O. Simell, J. Neu, C. H. Wasserfall, D. Schatz, M. A. Atkinson, and E. W. Triplett. 2010. Toward defining the autoimmune microbiome for T1D. ISME J.
19. Graham, S., P. Courtois, W. J. Malaisse, J. Rozing, F. W. Scott, and A. M. Mowat. 2004. Enteropathy precedes T1D in the BB rat. *Gut* 53: 1437-1444.
20. Grainger J R, Hall J A, Bouladoux N, Oldenhove G & Belkaid Y (2010) Microbe-dendritic cell dialog controls regulatory T-cell fate. Immunol Rev 234: 305-316.
21. Grinberg-Bleyer, Y., A. Baeyens, S. You, R. Elhage, G. Fourcade, S. Gregoire, N. Cagnard, W. Carpentier, Q. Tang, J. Bluestone, L. Chatenoud, D. Klatzmann, B. L. Salomon, and E. Piaggio. 2010. IL-2 reverses established T1D in NOD mice by a local effect on pancreatic regulatory T cells. *J. Exp. Med.* 207: 1871-1878.
22. Happel, K. I., P. J. Dubin, M. Zheng, N. Ghilardi, C. Lockhart, L. J. Quinton, A. R. Odden, J. E. Shellito, G. J. Bagby, S. Nelson, and J. K. Kolls. 2005. Divergent roles of IL-23 and IL-12 in host defense against *Klebsiella pneumoniae*. *J. Exp. Med.* 202: 761-769.
23. Higgins, S. C., A. G. Jarnicki, E. C. Lavelle, and K. H. Mills. 2006. TLR4 mediates vaccine-induced protective cellular immunity to *Bordetella pertussis*: role of IL-17-producing T cells. *J. Immunol.* 177: 7980-7989.
24. Hyttinen, V., J. Kaprio, L. Kinnunen, M. Koskenvuo, and J. Tuomilehto. 2003. Genetic liability of T1D and the onset age among 22,650 young Finnish twin pairs: a nationwide follow-up study. *Diabetes* 52: 1052-1055.
25. Inaba, K. and M. Inaba. 2005. Antigen recognition and presentation by DC. *Int. J. Hematol.* 81: 181-187.
26. Ivanov, I. I., L. Frutos Rde, N. Manel, K. Yoshinaga, D. B. Rifkin, R. B. Sartor, B. B. Finlay, and D. R. Littman. 2008. Specific microbiota direct the differentiation of IL-17-producing T-helper cells in the mucosa of the small intestine. Cell. Host Microbe 4: 337-349.
27. Jacob, C. O., S. Aiso, S. A. Michie, H. O. McDevitt, and H. Acha-Orbea. 1990. Prevention of diabetes in nonobese diabetic mice by tumor necrosis factor (TNF): similarities between TNF-alpha and interleukin 1 Proc. Natl. Acad. Sci. U.S.A 87: 968-972.
28. Kriegel, M. A., E. Sefik, J. A. Hill, H. J. Wu, C. Benoist, and D. Mathis. 2011. Naturally transmitted segmented filamentous bacteria segregate with diabetes protection in nonobese diabetic mice. *Proc. Natl. Acad. Sci. U.S.A* 108: 11548-11553.

29. Kunisawa, J. and H. Kiyono. 2011. Peaceful mutualism in the gut: revealing key commensal bacteria for the creation and maintenance of immunological homeostasis. *Cell. Host Microbe* 9: 83-84.

30. LaGasse, J. M. et al. 2002. Diabetes Care 25:505-511.

31. Larkin J., Ahmed C. M., Wilson T. D., and Johnson H. M. 2013. Regulation of interferon gamma signaling by suppressors cytokine signaling and regulatory T cells. *Frontiers in Immunol.* 18; 4:469.

32. Lau K, et al. (2011) Inhibition of type 1 diabetes correlated to a *lactobacillus johnsonii* N6.2-mediated Th17 bias. J Immunol 186: 3538-3546.

33. Like A A, Guberski D L, Butler L. (1991) Influence of environmental viral agents on frequency and tempo of diabetes-mellitus in BB/WOR rats. Diabetes 40: 259-262.

34. Martin E W [1995] Easton Pa., Mack Publishing Company, 19$^{th}$ ed.

35. Martin-Orozco, N., Y. Chung, S. H. Chang, Y. H. Wang, and C. Dong. 2009. Th17 cells promote pancreatic inflammation but only induce diabetes efficiently in lymphopenic hosts after conversion into Th1 cells. *Eur. J. Immunol.* 39: 216-224.

36. Matsuzaki T, Nagata Y, Kado S, Uchida K, Kato I, Hashimoto S, Yokokura T. (1997) Prevention of onset in an insulin-dependent diabetes mellitus model, NOD mice, by oral feeding of *Lactobacillus casei*. APMIS 105: 643-649.

37. McInerney M F, Pek S B, Thomas D W (1991) Prevention of insulitis and diabetes onset by treatment with complete Freund's adjuvant in NOD mice. Diabetes 40:715-725.

38. Meddings, J. B., J. Jarand, S. J. Urbanski, J. Hardin, and D. G. Gall. 1999. Increased gastrointestinal permeability is an early lesion in the spontaneously diabetic BB rat. *Am. J. Physiol.* 276: G951-7.

39. Metcalfe, K. A., G. A. Hitman, R. E. Rowe, M. Hawa, X. Huang, T. Stewart, and R. D. Leslie. 2001. Concordance for T1D in identical twins is affected by insulin genotype. *Diabetes Care* 24: 838-842.

40. Murphy, C. A., C. L. Langrish, Y. Chen, W. Blumenschein, T. McClanahan, R. A. Kastelein, J. D. Sedgwick, and D. J. Cua. 2003. Divergent pro- and antiinflammatory roles for IL-23 and IL-12 in joint autoimmune inflammation. *J. Exp. Med.* 198: 1951-1957.

41. Neu, J., C. M. Reverte, A. D. Mackey, K. Liboni, L. M. Tuhacek-Tenace, M. Hatch, N. Li, R. A. Caicedo, D. A. Schatz, and M. Atkinson. 2005. Changes in intestinal morphology and permeability in the biobreeding rat before the onset of T1D. *J. Pediatr. Gastroenterol. Nutr.* 40: 589-595.

42. Nikoopour, E., J. A. Schwartz, K. Huszarik, C. Sandrock, O. Krougly, E. Lee-Chan, and B. Singh. 2010. Th17 polarized cells from nonobese diabetic mice following mycobacterial adjuvant immunotherapy delay T1D. *J. Immunol.* 184: 4779-4712.

43. Ouyang, W., J. K. Kolls, and Y. Zheng. 2008. The biological functions of T helper 17 cell effector cytokines in inflammation. *Immunity* 28: 454-467.

44. Prochazka, M., D. V. Serreze, W. N. Frankel, and E. H. Leiter. 1992. NOR/Lt mice: MHC-matched diabetes-resistant control strain for NOD mice. *Diabetes* 41: 98-106.

45. Pyke, D. A., 1979. "Diabetes: the genetic connections." Diabetologia 17: 333-343

46. Redondo, M. J., L. Yu, M. Hawa, T. Mackenzie, D. A. Pyke, G. S. Eisenbarth, and R. D. Leslie. 2001. Heterogeneity of type I diabetes: analysis of monozygotic twins in Great Britain and the United States. *Diabetologia* 44: 354-362.

47. Roesch, L. F., G. L. Lorca, G. Casella, A. Giongo, A. Naranjo, A. M. Pionzio, N. Li, V. Mai, C. H. Wasserfall, D. Schatz, M. A. Atkinson, J. Neu, and E. W. Triplett. 2009. Culture-independent identification of gut bacteria correlated with the onset of diabetes in a rat model. ISME J. 3: 536-548.

48. Round, J. L. and S. K. Mazmanian. 2010. Inducible Foxp3$^+$ regulatory T-cell development by a commensal bacterium of the intestinal microbiota. Proc. Natl. Acad. Sci. U.S.A 107: 12204-12209.

49. Rubinstein, P. et al. 1981. *Hum. Immunol.* 3:271-275.

50. Sacks, D. B. et al. 2001. *J. Clin. Chem.* 47:803-804; Kawasaki, E. et al. 2000. *Front Biosci.* 5:E181-E190.

51. Sadelain M W J, Qin H Y, Lauzon J, Singh B. 1990a. Prevention of type-1 diabetes in NOD mice by adjuvant immunotherapy. Diabetes 39:583-589.

52. Sadelain M W J, Qin H Y, Sumoski W, Parfeny N, Singh B, Rabinovitch A. 1990b. Prevention of diabetes in the BB rat by early immunotherapy using Freund adjuvant. J Autoimmunity 3:671-680.

53. Sartorius, R., C. Bettua, L. D'Apice, A. Caivano, M. Trovato, D. Russo, I. Zanoni, F. Granucci, D. Mascolo, P. Barba, G. Del Pozzo, and P. De Berardinis. 2011. Vaccination with filamentous bacteriophages targeting DEC-205 induces DC maturation and potent anti-tumor T-cell responses in the absence of adjuvants. *Eur. J. Immunol.* 41: 2573-2584.

54. Schwartz, R F, Neu J, Schatz D, Atkinson M A, Wasserfall C (2007) Comment on: Brugman S et al. (2006) Antibiotic treatment partially protects against type 1 diabetes in the Bio-Breeding diabetes-prone rat. Is the gut flora involved in the development of type 1 diabetes? Diabetologia 49: 2105-2108. Diabetologia 50: 220-221.

55. Serreze, D. V., H. R. Gaskins, and E. H. Leiter. 1993. Defects in the differentiation and function of antigen presenting cells in NOD/Lt mice. *J. Immunol.* 150: 2534-2543.

56. Serreze, D. V., M. Prochazka, P. C. Reifsnyder, M. M. Bridgett, and E. H. Leiter. 1994. Use of recombinant congenic and congenic strains of NOD mice to identify a new insulin-dependent diabetes resistance gene. *J. Exp. Med.* 180: 1553-1558.

57. Shoda, L. K., D. L. Young, S. Ramanujan, C. C. Whiting, M. A. Atkinson, J. A. Bluestone, G. S. Eisenbarth, D. Mathis, A. A. Rossini, S. E. Campbell, R. Kahn, and H. T. Kreuwel. 2005. A comprehensive review of interventions in the NOD mouse and implications for translation. *Immunity* 23: 115-126.

58. Shrimpton, R. E., M. Butler, A. S. Morel, E. Eren, S. S. Hue, and M. A. Ritter. 2009. CD205 (DEC-205): a recognition receptor for apoptotic and necrotic self. *Mol. Immunol.* 46: 1229-1239.

59. Srikanta, S. 1984. "Pre-type 1 diabetes, linear loss of beta cell response to intravenous glucose," *Diabetes* 33: 717-720.

60. Steinman, R. M., D. Hawiger, K. Liu, L. Bonifaz, D. Bonnyay, K. Mahnke, T. Iyoda, J. Ravetch, M. Dhodapkar, K. Inaba, and M. Nussenzweig. 2003. DC function in vivo during the steady state: a role in peripheral tolerance. Ann. N. Y. Acad. Sci. 987: 15-25.

61. Stockinger, B., C. Bourgeois, and G. Kassiotis. 2006. CD4+ memory T cells: functional differentiation and homeostasis. *Immunol. Rev.* 211: 39-48.
62. Stratmann, T., N. Martin-Orozco, V. Mallet-Designe, L. Poirot, D. McGovern, G. Losyev, C. M. Dobbs, M. B. Oldstone, K. Yoshida, H. Kikutani, D. Mathis, C. Benoist, K. Haskins, and L. Teyton. 2003. Susceptible MHC alleles, not background genes, select an autoimmune T cell reactivity. *J. Clin. Invest.* 112: 902-914.
63. Suzuki T, Yamada T, Fujimura T, Kawamura E, Shimizu M Yamashita R. (1987) Diabetogenic effects of lymphocyte transfusion on the NOD or NOD nude mouse. In "Immune-Deficient Animals in Biomedical Research, Copenhagen, 1985", Rygaard, Brunner N, Groem N, Spang-Thomsen M, eds, pp 112-116, Karger, Basel.
64. Tse, H. M., T. C. Thayer, C. Steele, C. M. Cuda, L. Morel, J. D. Piganelli, and C. E. Mathews. 2010. NADPH oxidase deficiency regulates Th lineage commitment and modulates autoimmunity. *J. Immunol.* 185: 5247-5258.
65. Turley, S. J., J. W. Lee, N. Dutton-Swain, D. Mathis, and C. Benoist. 2005. Endocrine self and gut non-self intersect in the pancreatic L N. *Proc. Natl. Acad. Sci. U.S.A* 102: 17729-17733.
66. Vaarala, O., M. A. Atkinson, and J. Neu. 2008. The "perfect storm" for T1D: the complex interplay between intestinal microbiota, gut permeability, and mucosal immunity. *Diabetes* 57: 2555-2562.
67. Valladares, R., D. Sankar, N. Li, E. Williams, K. K. Lai, A. S. Abdelgeliel, C. F. Gonzalez, C. H. Wasserfall, J. Larkin, D. Schatz, M. A. Atkinson, E. W. Triplett, J. Neu, and G. L. Lorca. 2010. *Lactobacillus johnsonii* N6.2 mitigates the development of T1D in BB-DP rats. *PLoS One* 5: e10507.
68. Verdaguer, J., A. Amrani, B. Anderson, D. Schmidt, and P. Santamaria. 1999. Two mechanisms for the non-MHC-linked resistance to spontaneous autoimmunity. *J. Immunol.* 162: 4614-4626.
69. Waiboci L. W., Johnson H. M., Martin J. P., and Ahmed C. M. 2007a. Properties of a SOCS1 small molecule antagonist, J of Immunol., 178:94.1.
70. Waiboci L. W., Ahmed C. M., Mustafa G. M., Lawrence O. F., James P. M., Mohammed I. H., and Howard M. J. 2007b. Both the suppressor of cytokine signaling 1 (SOCS1) kinase inhibitory region and SOCS1 mimetic bind to JAK2 autophosphorylation site: implications for the development of a SOCS1 antagonist. *J Immunol.* 178:5058-5068.
71. Wicker L S, Miller B J, Coker L Z, McNally S E, Scott S, Mullen Y, Appel M C (1987) Genetic control of diabetes and insulitis in the nonobese diabetic (NOD) mouse. J Exp Med 165:1639-1654.
72. Yadav H, Shalini J, Sinha P R (2007) Antidiabetic effect of probiotic dahi containing *Lactobacillus acidophilus* and *Lactobacillus casei* in high fructose fed rats. Nutrition 23: 62-68.
73. Zipris, D. 2009. Epidemiology of T1D and what animal models teach us about the role of viruses in disease mechanisms. *Clin. Immunol.* 131: 11-23.

We claim:

1. A method of treating or preventing type 1 Diabetes (TID), the method comprising administering to a human who has been diagnosed as having diabetes, or at risk for diabetes, an antigen presenting cell (APC) contacted with a suppressor of cytokine signaling-1 (SOCS1) protein peptide or mimetic inhibitor that antagonizes the activity of SOCS1 protein, wherein said contacting confers upon the APC the ability to inhibit the generation of diabetogenic T cells.

2. The method of claim 1, wherein the APC is a dendritic cell (DC).

3. The method of claim 1, wherein the peptide is selected from the group consisting of SOCS1-kinase inhibitory region (SOCS1-KIR) peptide, SOCS1-KIR2A, Tyrosine Kinase Inhibitory Peptide (TKIP), SOCS1-KIR dimer, JAK2 (1001-1013), and pJAK2(1001-1013).

* * * * *